(12) United States Patent
Schlingensiepen et al.

(10) Patent No.: US 8,629,117 B2
(45) Date of Patent: Jan. 14, 2014

(54) METHOD FOR STIMULATING THE IMMUNE SYSTEM

(75) Inventors: Karl-Hermann Schlingensiepen, Göttingen (DE); Reimar Schlingensiepen, Göttingen (DE); Wolfgang Brysch, Göttingen (DE)

(73) Assignee: Biognostik Gesellschaft fur biomolekulare Diagnostik mbH, Göttingen (DE)

(*) Notice: Subject to any disclaimer, the term of this patent is extended or adjusted under 35 U.S.C. 154(b) by 202 days.

(21) Appl. No.: 11/898,080

(22) Filed: Sep. 7, 2007

(65) Prior Publication Data

US 2008/0124301 A1   May 29, 2008

(30) Foreign Application Priority Data

Jun. 10, 1998 (EP) .................................. 98110709
Jul. 25, 1998 (EP) .................................. 98113974

(51) Int. Cl.
*A01N 43/04* (2006.01)
*C12Q 1/68* (2006.01)
*C12P 19/34* (2006.01)
*C07H 21/02* (2006.01)
*C07H 21/04* (2006.01)

(52) U.S. Cl.
USPC ............. 514/44; 435/6; 435/91.1; 435/91.31; 435/455; 514/1; 514/2; 536/23.1; 536/24.31; 536/24.5

(58) Field of Classification Search
USPC .......... 435/6, 91.1, 91.31, 375, 455; 514/1, 2, 514/44; 536/23.1, 24.5, 23.5, 24.31
See application file for complete search history.

(56) References Cited

U.S. PATENT DOCUMENTS

| | | | |
|---|---|---|---|
| 5,891,858 A | 4/1999 | Rubenstein | |
| 6,045,802 A * | 4/2000 | Schlom et al. | 424/199.1 |
| 6,376,199 B1 | 4/2002 | Caniggia et al. | 435/7.2 |
| 6,455,689 B1 | 9/2002 | Schlingensiepen et al. | 536/24.5 |
| 6,468,986 B1 * | 10/2002 | Zuckermann et al. | 514/44 R |

FOREIGN PATENT DOCUMENTS

| | | |
|---|---|---|
| EP | 0542679 | 5/1993 |
| JP | 10052285 | 2/1998 |
| WO | WO 94/08053 | 4/1994 |
| WO | WO 94/25588 | * 11/1994 |
| WO | WO 94/29452 | 12/1994 |
| WO | WO 95/00103 | 1/1995 |
| WO | WO 96/02143 | 2/1996 |
| WO | WO 96/23065 | 8/1996 |
| WO | WO 97/39120 | 10/1997 |
| WO | WO 99/50411 | 10/1999 |

OTHER PUBLICATIONS

Kingsley, D.M., Genes & Development, vol. 8, pp. 133-146 (1994).*
Wojtowicz-Praga, S. (1996).Modulation of B16 Melanoma Growth and Metastasis by Anti-Transforming Growth Factor β Antibody and Interleukin-2. *Journal of Immunotherapy.* 19, 169-175.
Fitzpatrick, D (1994).Transforming Growth Factor-Beta: Antisense RNA-Mediated Inhibition Affects Anchorage-Independent Growth, Tumorigenicity and Tumor-Infiltrating T-Cells in Malignant Mesothelioma. *Growth Factors.* 11, 29-44.
Piotr Jachimczak et al., "The Effect of Transforming Growth Factor-$β_2$ Specific Phosphorothioate-anti-sense Oligodeoxynucleotides in Reversing Cellular immunosuppression in Malignant Glioma", vol. 78, pp. 944-951, Jun. 1993.
Maureen Spearman et al., "Antisense Oligodeoxyribonucleotide Inhibition of TGF-$β_1$ Gene Expression and Alterations in the Growth and malignant Properties of mouse Fibrosarcoma Cells", vol. 149, No. 1, pp. 25-29, Nov. 1994.
XP-000886176, "Concomitant Expression of Interferon-γ and Antisense TGF-β Transgenes Enhances the Immunogenicity of a Murine Mammary Carcinoma", Nov. 1997.
Fakhrai, H. et al. Proc. Natl. Acad. Sci. vol. 93, pp. 2909-2914 (1996).
Peracchi, A. et al. Rev. Med. Virol. vol. 14, pp. 47-64 (2004).
Pihl-Carey, K BioWorld Today. vol. 10, pp. 1-2 (1999).
Crooke, S. Antisense Res. and Application, pp. 1-50 (ed. by S. Crooke). Springer-Verlag (1999).
Branch, A. Trends in Biochem. Sci. vol. 23, pp. 45-50 (1998).
Palu, G. et al. J. Biotech. vol. 68, pp. 1-13 (1999).
Chirila, T. et al. Biomaterials, vol. 23, pp. 321-342 (2002).
Agrawal, S. et al. Molecular Med. Today. vol. 6, pp. 72-81 (2000).
Tamm, I. et al. The Lancet, vol. 358, pp. 489-497 (2001).

* cited by examiner

*Primary Examiner* — Jane Zara
(74) *Attorney, Agent, or Firm* — Jacobson Holman PLLC

(57) ABSTRACT

Medicament comprising a combination of
  at least one inhibitor of the effect of a substance negatively effecting an immune response, the substance selected from the group consisting of TGF-β and its receptors, VEGF and its receptors, interleukin 10 (IL-10) and its receptors, $PGE_2$ and its receptors, wherein the inhibitor has a molecular weight of less than 100 kDa and
  at least one stimulator positively effecting an immune response.

6 Claims, 11 Drawing Sheets

| | | |
|---|---|---|
| 1. | TGF-ß2-1 | C ACA CAG TAG TGC A |
| 2. | TGF-ß2-2 | GC ACA CAG TAG TGC |
| 3. | TGF-ß2-3 | GC TTG CTC AGG ATC TGC |
| 4. | TGF-ß2-4 | TAC TCT TCG TCG CT |
| 5. | TGF-ß2-5 | C TTG GCG TAG TAC T |
| 6. | TGF-ß2-6 | G TAA ACC TCC TTG G |
| 7. | TGF-ß2-7 | GT CTA TTT TGT AAA CCT CC |
| 8. | TGF-ß2-8 | GC ATG TCT ATT TTG TAA ACC |
| 9. | TGF-ß2-9 | CGG CAT GTC TAT TTT GTA |
| 10. | TGF-ß2-10 | G GCA TCA AGG TAC C |
| 11. | TGF-ß2-11 | CTG TAG AAA GTG GG |
| 12. | TGF-ß2-12 | AC AAT TCT GAA GTA GGG T |
| 13. | TGF-ß2-13 | T CAC CAA ATT GGA AGC AT |
| 14. | TGF-ß2-14 | GCT TTC ACC AAA TTG GAA GC |
| 15. | TGF-ß2-15 | CTG GCT TTT GGG TT |
| 16. | TGF-ß2-16 | T CTG ATA TAG CTC AAT CC |
| 17. | TGF-ß2-17 | T CCT AGT GGA CTT TAT AG |
| 18. | TGF-ß2-18 | T TTT TCC TAG TGG ACT |
| 19. | TGF-ß2-19 | C AAT TAT CCT GCA CAT TTC |
| 20. | TGF-ß2-20 | GC AAT TAT CCT GCA CA |
| 21. | TGF-ß2-21 | GC AGC AAT TAT CCT GC |
| 22. | TGF-ß2-22 | TG GCA TTG TAC CCT |
| 23. | TGF-ß2-23 | TG TGC TGA GTG TCT |
| 24. | TGF-ß2-24 | CC TGC TGT GCT GAG TG |
| 25. | TGF-ß2-25 | C TTG GGT GTT TTG C |
| 26. | TGF-ß2-26 | T TTA GCT GCA TTT GCA AG |
| 27. | TGF-ß2-27 | G CCA CTT TTC CAA G |
| 28. | TGF-ß2-14/1 | CTT TCA CCA AAT TGG AAG |
| 29. | TGF-ß2-14/2 | CAC CAA ATT GGA AGC |
| 30. | TGF-ß2-14/3 | TCA CCA AAT TGG AAG C |
| 31. | TGF-ß2-15/1 | CTC TGG CTT TTG GG |
| 32. | TGF-ß2-9/1 | CGG CAT GTC TAT TTT G |
| 33. | TGF-ß1-1 | CGA TAG TCT TGC AG |
| 34. | TGF-ß1-2 | GTC GAT AGT CTT GC |
| 35. | TGF-ß1-3 | CTT GGA CAG GAT CT |
| 36. | TGF-ß1-4 | CCA GGA ATT GTT GC |
| 37. | TGF-ß1-5 | CCT CAA TTT CCC CT |
| 38. | TGF-ß1-6 | GAT GTC CAC TTG CA |
| 39. | TGF-ß1-7 | CTC CAA ATG TAG GG |
| 40. | TGF-ß1-8 | ACC TTG CTG TAC TG |
| 41. | TGF-ß1-9 | GTA GTA CAC GAT GG |
| 42. | TGF-ß1-10 | CAC GTA GTA CAC GA |
| 43. | TGF-ß1-11 | CAT GTT GGA CAG CT |
| 44. | TGF-ß1-12 | GCA CGA TCA TGT TG |
| 45. | TGF-ß1-13 | TGT ACT CTG CTT GAA C |
| 46. | TGF-ß1-14 | CTG ATG TGT TGA AGA ACA |
| 47. | TGF-ß1-15 | CTC TGA TGT GTT GAA G |
| 48. | TGF-ß1-16 | GGA AGT CAA TGT ACA G |
| 49. | TGF-ß1-17 | CAT GTC GAT AGT CTT GCA |
| 50. | TGF-ß1-18 | AGC TGA AGC AAT AGT TGG |
| 51. | TGF-ß1-19 | GTC ATA GAT TTC GTT GTG |
| 52. | TGF-ß1-20 | CTC CAC TTT AAC TT GAG |
| 53. | TGF-ß1-21 | TGC TGT ATT TCT GGT ACA |
| 54. | TGF-ß1-137 | CGA TAG TCT TGC AG |

Fig. 1-1

| | | |
|---|---|---|
| 55. | b1-N17 | TCC TCT TCG ACT GCT CTC |
| 56. | b2-N14 | CGA AGG TTA AAC CAC TTT CG |
| 57. | b2-N24 | GTG AGT CGT GTC GTC C |
| | | |
| 58. | TGF-ß2-98-1 | CATCGTTGTCGTCG |
| 59. | TGF-ß2-98-2 | CGCTTCTTCCGCCG |
| 60. | TGF-ß2-98-3 | CGAAGGAGAGCCATTCG |
| 61. | TGF-ß2-98-4 | CGATGTAGCG |
| 62. | TGF-ß2-98-5 | CGTCAAATCG |
| 63. | TGF-ß2-98-6 | CGTAGTACTCTTCGTCG |
| 64. | TGF-ß2-98-7 | CGCGCTCGCAGGCG |
| 65. | TGF-ß2-98-8 | CGGCCGCCCTCCGGCTCG |
| 66. | TGF-ß2-98-9 | CGCGGATCGCCTCG |
| 67. | TGF-ß2-98-10 | GAGCGCGACCGTGAC |
| | | |
| 68. | TGF-ß-17-c-2260 | ACC TCC TTG GCG TAG TA |
| 69. | TGF-ß-12-9/20-2261 | AGG GCG GCA TGT CTA TTT TG |
| 70. | TGF-ß-123-2262 | CAG AAG TTG GCA TTG TAC |
| 71. | TGF-ß-12-9/22-2263 | AGG GCG GCA TGT CTA TTT TGT A |
| 72. | TGF-ß-23-2268 | TGG GAC ACG CAG CAA GG |
| | | |
| 73. | TGF-ß1-98-1 | CGGGGGCGGGGCGGGG |
| 74. | TGF-ß1-98-2 | CGGGGCGGGGCGGGGCG |
| 75. | TGF-ß1-98-3 | CGGCGCCGCCGAGGCGCCCG |
| 76. | TGF-ß1-98-4 | CCGAGGTCCTTGCGG |
| 77. | TGF-ß1-98-5 | CGGCGGTGCCGGGA |
| 78. | TGF-ß1-98-6 | CTCGGCGGCCGGTAG |
| 79. | TGF-ß1-98-7 | CGCTAAGGCG |
| 80. | TGF-ß1-98-8 | CCGCACAACTCCGG |
| 81. | TGF-ß1-98-9 | GCGAGTCGCTGG |
| 82. | TGF-ß1-98-10 | CGGTTGCTGAGGTATCG |
| 83. | TGF-ß1-98-11 | CCGGGAGAGCAACACGG |
| 84. | TGF-ß1-98-12 | CGCTTCTCG |
| 85. | TGF-ß1-98-13 | CCATTAGCACGCGGG |
| 86. | TGF-ß1-98-14 | CGGGCTCCG |
| 87. | TGF-ß1-98-15 | CCGGCCACCCGGTCGCGG |
| 88. | TGF-ß1-98-16 | CGAGCACGGCCTCG |
| 89. | TGF-ß1-98-17 | CGGGCAGCGGGCCGGGCG |
| 90. | TGF-ß1-98-18 | CGCGGATGGCCTCG |
| 91. | TGF-ß1-98-19 | CGATGCGCTTCCG |
| 92. | TGF-ß1-98-20 | CCCGCGGCCGGCGGG |
| 93. | TGF-ß1-98-21 | CGCAGCCCGGAGGGCG |
| 94. | TGF-ß1-98-22 | CGGCGCCCCCG |
| 95. | TGF-ß1-98-23 | CGGCACTGCCGAGAGCGCG |
| 96. | TGF-ß1-98-24 | CGGGGATGAAGGCGGCG |
| 97. | TGF-ß1-98-25 | CGGGTCGGCGACTCCCG |
| 98. | TGF-ß1-98-26 | CGCCTGAGGGACGCCG |
| 99. | TGF-ß1-98-27 | AAGCGTCCCCGGCG |
| 100. | TGF-ß1-98-28 | CGCGGGGCAGCGTCGCG |
| 101. | TGF-ß1-98-29 | CCCCGCGCCTCCGG |
| 102. | TGF-ß1-98-30 | CGGCGGCGGCTCG |
| 103. | TGF-ß1-98-31 | CGCTCCGGGCCGAGGCCG |
| 104. | TGF-ß1-98-32 | CGGCCCCGCGGGCG |
| 105. | TGF-ß1-98-33 | CGGACGGGGCGTCC |
| 106. | TGF-ß1-98-34 | CGGCCGGGGCCCTCG |

Fig. 1-2

| | | |
|---|---|---|
| 107. | TGF-ß3-98-1 | TCGAGCTTCCCCGA |
| 108. | TGF-ß3-98-2 | CCCGGAGCCGAAGG |
| 109. | TGF-ß3-98-3 | CCCGAGGAGCGGG |
| 110. | TGF-ß3-98-4 | ACGCAGCAAGGCGA |
| 111. | TGF-ß3-98-5 | CGGGTTGTCGAGCCG |
| 112. | TGF-ß3-98-6 | CGGCAGTGCCCCG |
| 113. | TGF-ß3-98-7 | CGGAATTCTGCTCG |
| 114. | TGF-ß3-98-8 | TTCGTTGTGCTCCG |
| 115. | TGF-ß3-98-9 | ATTCCGACTCGGTG |
| 116. | TGF-ß3-98-10 | ACGTGGGTCATCACCGT |
| 117. | TGF-ß3-98-11 | CGAAGAAGCG |
| 118. | TGF-ß3-312 | CCT AAT GGC TTC CA |
| 119. | VEGF-98-1 | CGGCCGCGGTGTGT |
| 120. | VEGF-98-2 | CGGGAATGCTTCCGCCG |
| 121. | VEGF-98-3 | CGGCTCACCGCCTCGGC |
| 122. | VEGF-98-4 | CACGTCTGCGGATC |
| 123. | VEGF-98-5 | CCCCGCATCGCATCAGGG |
| 124. | VEGF-98-6 | CGCCTTGCAACGCG |
| 125. | VEGF-98-7 | CCGACCGGGGCCGG |
| 126. | VEGF-49 | GTTCATGGTTTCGG |
| 127. | VEGF-55 | GCAGAAAGTTCATGG |
| 128. | VEGF-188 | GCTGATAGACATCC |
| 129. | VEGF-190 | GCGCTGATAGACAT |
| 130. | VEGF-194 | GTAGCTGCGCTGATAG |
| 131. | VEGF-253 | CTCGATCTCATCAG |
| 132. | VEGF-255 | ATGTACTCGATCTCATC |
| 133. | VEGF-260 | GAAGATGTACTCGATC |
| 134. | VEGF-263 | CTTGAAGATGTACTCG |
| 135. | VEGF-292 | GCATCGCATCAGGG |
| 136. | VEGF-294 | CCGCATCGCATCAG |
| 137. | VEGF-422 | CATTGTTGTGCTGTAGG |
| 138. | VEGF-434 | GGTCTGCATTCACATTTG |
| 139. | VEGF-441 | CTTTGGTCTGCATTC |
| 140. | VEGF-445 | CTTTCTTTGGTCTGC |
| 141. | VEGF-450 | GCTCTATCTTTCTTTGG |
| 142. | VEGF-455 | GTCTTGCTCTATCTTTC |
| 143. | VEGF-459 | CTTGTCTTGCTCTATC |
| 144. | VEGF-596 | CATCTGCAAGTACGTTCG |
| 145. | VEGF-598 | CACATCTGCAAGTACGTT |
| 146. | VEGF-600 | GTCACATCTGCAAGTACG |
| 147. | VEGF-600-2 | CATCTGCAAGTACG |
| 148. | VEGF-601 | CACATCTGCAAGTAC |
| 149. | VEGF-604 | GTCACATCTGCAAG |
| 150. | VEGF-607 | CTTGTCACATCTGC |
| 151. | VEGF-607-2 | GGCTTGTCACATCTGC |
| 152. | VEGF-610 | CTCGGCTTGTCACATC |
| 153. | VEGF-638 | CTCCTTCCTCCTGC |
| 154. | VEGF-766 | GCT TGA AGA TGT ACCT CG |
| 155. | VEGF-r-1062 | CGT TGC TCT CCG ACG |
| 156. | flt-1165 | GAC ACG GCC TTT TCG |
| 157. | flt-rm-2115 | CCA GCA GCT GAC CAT GG |
| 158. | flk1/kdr-m-2315 | GAA ATC GAC CCT CGG |
| 159. | MCP-1-Rec-A/B-571 | GCA TGT TGT GGA TG |
| 160. | MCP-1-1954 | GCA GAG ACT TTC ATG C |
| 161. | MCP-1-1955 | ATA ACA GCA GGT GAC TGG |

Fig. 1-3

| | | |
|---|---|---|
| 162. | MCP-1-1956 | GAA CCC ACT TCT GC |
| 163. | MCP-1-2761 | GAC ACT TGC TGC TG |
| 164. | MCP-1-2762 | CCA CTT CTG CTT GGG |
| 165. | VEGF-703 | CTG CAA GTA CGT TCG |
| 166. | flt-1567 | TCC CTT ATG ATG CCA GCA AGT G |
| 167. | TGF-ß-Rec-I-796 | CCA GCA ATG ACA GC |
| 168. | TGF-ß-1-rwk-1 | G GGA AAG CTG AGG C |
| 169. | TGF-ß-1-rwk-2 | T CGA GGG AAA GCT GA |
| 170. | TGF-ß-1-rwk-3 | C CTC GAG GGA AAG C |
| 171. | TGF-ß-1-rwk-4 | GG GCT GGT GTG GTG |
| 172. | TGF-ß-1-rwk-5 | GA ACA GGG CTG GTG TG |
| 173. | TGF-ß-1-rwk-6 | G AAC AGG GCT GGT G |
| 174. | TGF-ß-1-rwk-7 | AG AGC GCG AAC AGG |
| 175. | TGF-ß-1-rwk-8 | GA GAG CGC GAA CAG G |
| 176. | TGF-ß-1-rwk-9 | CGA GAG CGC GAA CAG |
| 177. | TGF-ß-1-rwk-10 | CCC CTG GCT CGG GGG |
| 178. | TGF-ß-1-rwk-11 | C CCT GGC TCG GGG |
| 179. | TGF-ß-1-rwk-12 | C CCC TGG CTC GGG G |
| 180. | TGF-ß-1-rwk-13 | TCC CCC TGG CTC GG |
| 181. | TGF-ß-1-rwk-14 | C TCC CCC TGG CTC G |
| 182. | TGF-ß-1-rwk-15 | TGC GCT TCC GCT TCA C |
| 183. | TGF-ß-1-rwk-16 | CC TCG ATG CGC TTC |
| 184. | TGF-ß-1-rwk-17 | G ATG GCC TCG ATG C |
| 185. | TGF-ß-1-rwk-18 | G GAT GGC CTC GAT GC |
| 186. | TGF-ß-1-rwk-19 | ATG GCC TCG ATG CGC TT |
| 187. | TGF-ß-3-rwk-1 | TC AGC AGG GCC AGG |
| 188. | TGF-ß-3-rwk-2 | GCA AAG TTC AGC AGG GC |
| 189. | TGF-ß-3-rwk-3 | GG CAA AGT TCA GCA GG |
| 190. | TGF-ß-3-rwk-4 | GT GGC AAA GTT CAG CAG G |
| 191. | TGF-ß-3-rwk-5 | GTG GCA AAG TTC AG |
| 192. | TGF-ß-3-rwk-6 | GAC CGT GGC AAA GTT CAG |
| 193. | TGF-ß-3-rwk-7 | AGA GAG GCT GAC CGT |
| 194. | TGF-ß-3-rwk-8 | GAC AGA GAG AGG CTG AC |
| 195. | TGF-ß-3-rwk-9 | A CAG AGA GAG GCT GA |
| 196. | TGF-ß-3-rwk-10 | GT GGA CAG AGA GAG G |
| 197. | TGF-ß-3-rwk-11 | CA AGT GGA CAG AGA GAG G |
| 198. | TGF-ß-3-rwk-12 | TCT TCT TGA TGT GGC C |
| 199. | TGF-ß-3-rwk-13 | CC CTC TTC TTC TTG ATG |
| 200. | TGF-ß-3-rwk-14 | C ACC CTC TTC TTC T |
| 201. | TGF-ß-3-rwk-15 | A TGG ATT TCT TTG GCA T |
| 202. | TGF-ß-3-rwk-16 | GGA TTT CTT TGG C |
| 203. | TGF-ß-3-rwk-17 | AA GTT GGA CTC TCT TCT C |
| 204. | TGF-ß-3-rwk-18 | TAA GTT GGA CTC TCT TCT |
| 205. | TGF-ß-3-rwk-19 | GAC CTA AGT TGG ACT C |
| 206. | TGF-ß-3-rwk-20 | T TTC TAG ACC TAA GTT GG |
| 207. | TGF-ß-3-rwk-21 | CT GAT TTC TAG ACC TAA G |
| 208. | TGF-ß-3-rwk-22 | G AAG CAG TAA TTG GTG T |
| 209. | TGF-ß-3-rwk-23 | GG AAT CAT CAT GAG G |
| 210. | TGF-ß-3-rwk-24 | GGG AAT CAT CAT GAG |
| 211. | TGF-ß-3-rwk-25 | G GTT GTC GAG CCG GT |
| 212. | TGF-ß-3-rwk-26 | GTC CTC CCA ACA TAG TA |
| 213. | TGF-ß-3-rwk-27 | GG GTC CTC CCA ACA |

Fig. 1-4

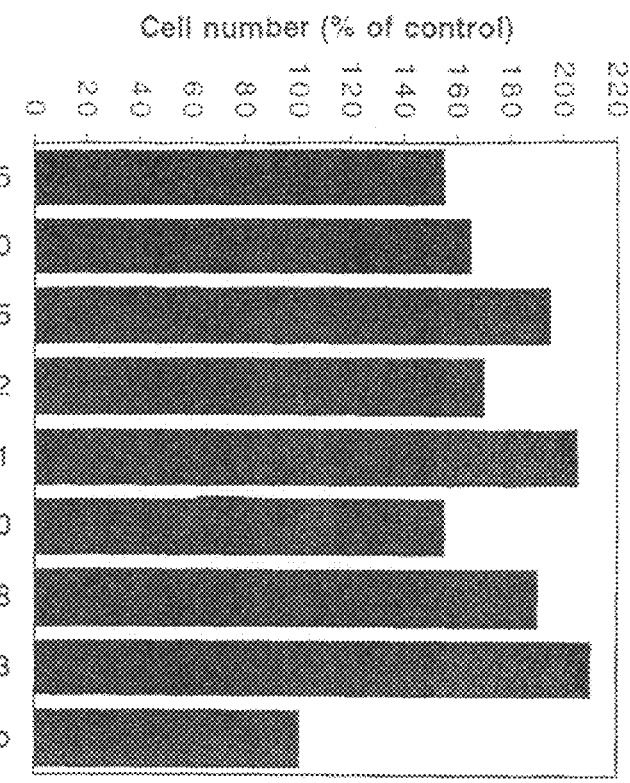
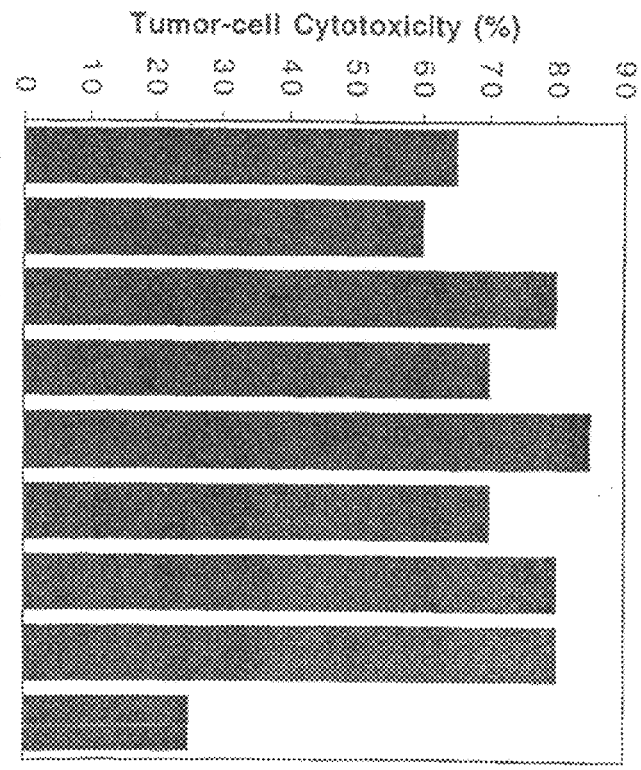
Figure 6

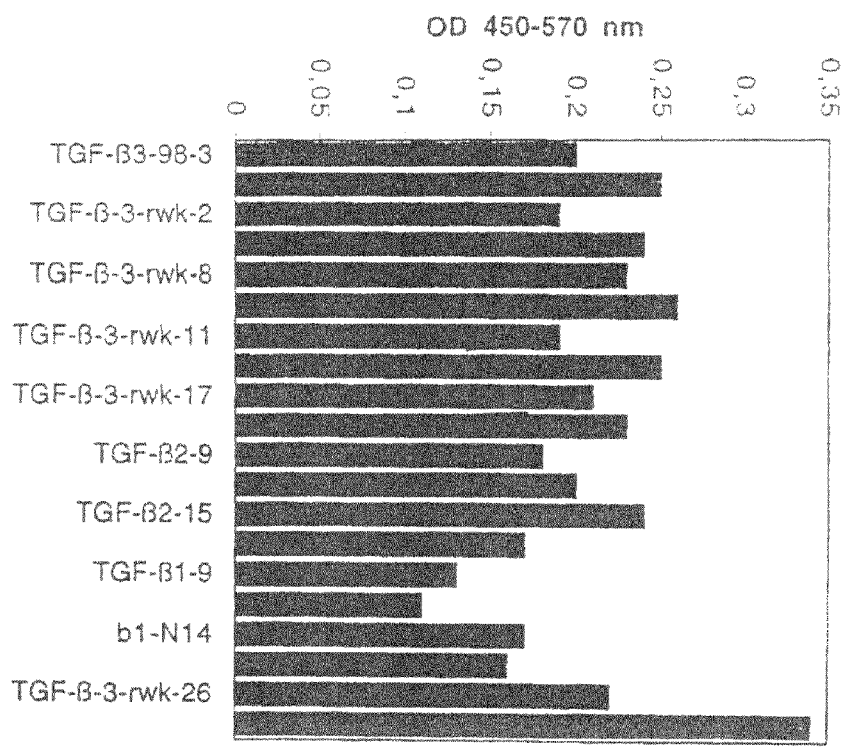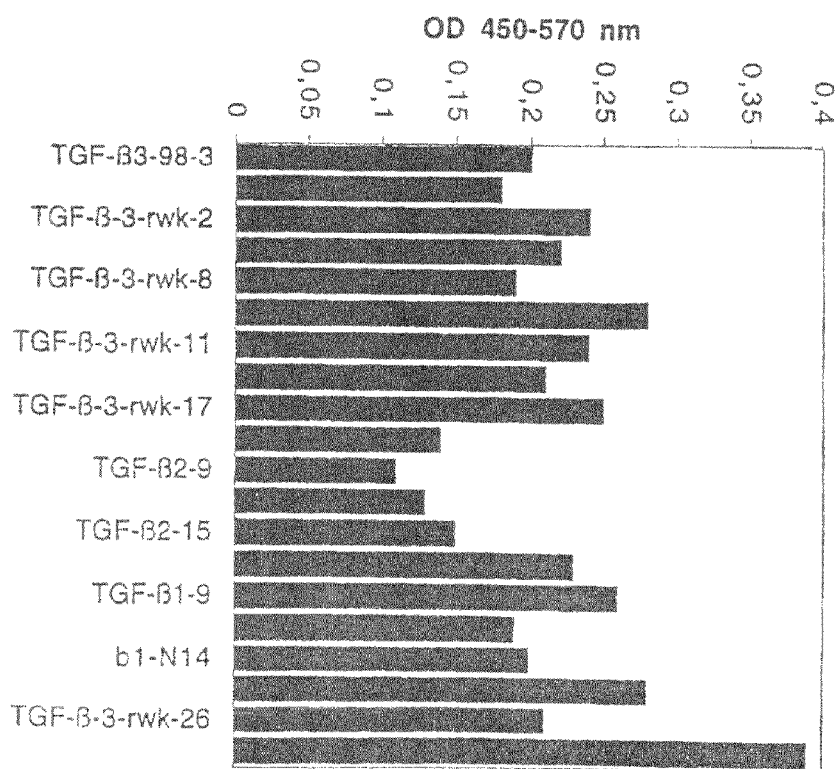
Figure 7

METHOD FOR STIMULATING THE IMMUNE SYSTEM

Two different approaches have been used in the prior art to enhance the immune response against neoplastic cells. One approach uses the addition of cytokines like interleukin-2 (IL-2) or transfection of tumor cells and/or immune cells with genes coding for cytokines like IL-2 or other proteins enhancing the immune response like transfection of tumor cells with lymphotactin or like transfection of T-lymphocytes with CD-40 Ligand.

The second approach uses the inhibition of immunosuppressive molecules to enhance the body's immune response to tumor cells. Thus, J. NEUROSURG. 78 (1993) 944-51, Jachimczak et al. (1993) and WO 94/25588, Schlingensiepen et al. (1994) teach the use of antisense oligonucleotides targeted to TGF-β to reverse tumor-induced immunosuppression.

Several documents in the prior art teach that a combination of these two approaches is either not efficacious or is not beneficial over use of one of the two approaches used alone.

Thus, CANCER BIOTHER. 8(2), 1993, 159-170, Gridley et al., as well as CANCER BIOTHER. 9(4), 1994, 317-327, Mao et al., both teach that a combination of anti-transforming growth factor-beta antibody with IL-2 does not cause significant antitumor effects.

Furthermore, PROC. NATL. ACAD. SCI 93, (1996), 2909-2914, Fakhrai et al., teaches that a combination of transfection with genes encoding antisense sequences to transforming growth factor beta (TGF-β) TGF-β mRNA with transfection of IL-2 into tumor cells does not increase the immune response against the tumor compared to transfection with TGF-β antisense alone.

Surprisingly, in contrast, certain combinations of stimulators and inhibitors are more efficacious than either approach alone.

The present invention discloses a medicament comprising a combination of
- at least one inhibitor of the effect of a substance negatively effecting an immune response, the substance selected from the group consisting of TGF-β and its receptors, VEGF and its receptors, interleukin 10 (IL-10) and its receptors, $PGE_2$ and its receptors, wherein the inhibitor has a molecular weight of less than 100 kDa and
- at least one stimulator positively effecting an immune response.

In a preferred embodiment, the inhibitor is inhibiting the synthesis or function of molecules suppressing or downregulating or negatively affecting the immune response. The inhibitor can be an oligonucleotide which may function as an antisense nucleotide or a ribozyme or it may be an antibody fragment derived from an anti-body e.g. a fab-fragment or a single chain antibody.

Preferably, the stimulator is positively effecting the immune response by increasing presentation of antigens and/or enhancing proliferation and/or function of immune cells.

In a preferred embodiment, the stimulator is enhancing the synthesis or function of molecules stimulating, enhancing, upregulating and/or positively regulating the immune response. In particular, the stimulator is stimulating and/or enhancing the synthesis and/or the function of factors such as GM-CSF, SCF, CSF, IFN-γ, FLT-3-ligand as well as monocyte chemotatic proteins (MCP-1), interleukin-2, interleukin-4, interleukin-12 and/or interleukin-18 or is one of the mentioned interleukins or is selected from the group consisting of viruses, viral antigens, antigens expressed in tumor cells or pathogens but not in normal cells, organspecific antigens expressed in affected organs which are not essential for the organism, e.g. prostate, ovary, breast, melanine producing cells.

The stimulators are preferably selected from
a) Chemokines, including lymphotactin and/or immune cell attracting substances and/or
b) viruses and/or parts of viruses, including retroviruses, adenoviruses, papillomaviruses, Epstein-Barr-Viruses, Viruses that are non-pathogenic including Newcastle-Disease virus, Cow-pox-virus and/or
c) autologous and/or heterologous MHC-Molecules and/or
d) molecules involved in antigen processing and/or
e) molecules involved in antigen presentation and/or
f) molecules involved in mediating immune cell effects and/or
g) molecules involved in mediating immune cell cytotoxic effects and/or
h) molecules involved in antigen transportation and/or
i) co-stimulatory molecules
j) peptides enhancing recognition by immune cells and/or cytotoxic effects of immune cells
k) the peptides containing one or more amino acids differing between a protein in the target cell from the other cells within an organism
l) the peptides according to j) being
   Peptides containing one or more mutations and/or amino acid substitutions of the ras protein amino and/or
   Peptides containing one or more mutations and/or amino acid substitutions of the p53 protein and/or
   Peptides containing one or more mutations and/or amino acid substitutions of the EGF-Receptor protein and/or
   Peptides containing one or more mutations and/or amino acid substitutions of fusion peptides and/or fusion proteins and/or
   Peptides containing one or more mutations and/or amino acid substitutions and/or amino acid substitutions caused by gene rearrangements and/or gene translocations and/or
   Peptides containing one or more mutations and/or amino acid substitutions of the retinoblastoma protein and/or
   Peptides containing one or more mutations and/or amino acid substitutions of proteins coded by oncogenes and/or protooncogenes and/or
   Peptides containing one or more mutations and/or amino acid substitutions of proteins coded by anti-oncogenes and/or tumor suppressor genes and/or
   Peptides derived from proteins differing in the target cell by one or more amino acids from the proteins expressed by other cells in the same organism and/or
   Peptides derived from viral antigens and/or coded by viral nucleic acids and/or
   Peptides derived from proteins expressed in a diseased organ but not in the nervous system, muscle, hematopoetic system or other organs essential for survival. Diseased organs are e.g. prostate, ovary, breast, melanine producing cells and the like.
m) tumor cell extracts and/or tumor cell lysates and/or adjuvants,
n) fusion cells of dendritic and tumor cells.

These fusion cells are hybridoma cells derived from a mixture of dentritic cells and tumor cells. Dentritic cells are generated e.g. by treatment of PBMC with GM-CSF and IL-4 or a mixture of GM-CSF, IL-4 and IFN-γ or FLT-3 ligand. Fusion of dendritic cells with tumor cells can be achieved e.g. using PEG (polyethylene glycole) or electrofusion.

Surprisingly, treatment of PBMC with VEGF-oligonucleotides enhanced the number and/or effectiveness of dendritic cells.

In one embodiment of the invention the inhibitor is an oligonucleotide. Preferably the oligonucleotides of FIG. 1 are useful in the medicament of the present invention.

In a further embodiment, the invention provides oligonucleotides having one of the sequences given in FIG. 1-2 to 1-4.

Also oligonucleotides having 1 to 10 additional-nucleotides at the 5'- or 3'-end are part of the invention.

Oligonucleotide sequences used for transfection are usually much longer sequences than those used for antisense oligonucleotides, which usually do not exceed 30 bases in length and are applied as short single-stranded sequences and are not integrated into a vector system.

Since transfected sequences are usually much longer than oligonucleotides, if cross inhibition of different members of a protein family would occur with the antisense technology, such cross inhibition of other mRNAs than the target mRNA, is much more likely with transfected antisense sequences, compared to oligonucleotides. However, Cell Growth Differ, Vol. 6(12), February 1995, pages 1635-1642, Huang, F. et al. teaches "only the K6 transfectant exhibited 39 and 33% respectively of the levels or TGF beta1 mRNA and active secreted TGF beta1 protein of the parental line. K6 exhibited no change in TGF beta2 expression and TGF beta3 expression was not detected in either parental or transfectant cell line."

It was therefore surprising to find oligonucleotides according to this invention, which were able to significantly reduce expression of both, TGF-$\beta_1$ as well as TGF-$\beta_2$ e.g. TGF-$\beta$1-14, TGF-$\beta$1-15, TGF-$\beta$-17-c-2260, TGF-$\beta$-123-2262, TGF-$\beta$-23-2268, TGF-$\beta$2-4, TGF-$\beta$2-14, TGF-$\beta$2-15, TGF-$\beta$2-9, TGF-$\beta$2-14/1, TGF-$\beta$2-14/2, TGF-$\beta$1-136. Furthermore surprisingly oligonucleotides were designed, which were able to significantly reduce expression of TGF-$\beta_2$ as well as TGF-$\beta_3$.

Surprisingly even oligonucleotides were found, which were able to significantly reduce expression of TGF-$\beta_2$ as well as TGF-$\beta_1$, and TGF-$\beta_3$, e.g. b1-N17, b1-N14, b1-N24, TGF-$\beta$2-9, TGF-$\beta$2-14, TGF-$\beta$-2-15, TGF-$\beta$-17-c-2260, TGF-$\beta$-12-9/20-2261, TGF-$\beta$-123-2262, TGF-$\beta$-12-9/22-2263, TGF-$\beta$-23-2268, TGF-$\beta$1-98-11, TGF-$\beta$1-98-23, TGF-$\beta$3-98-7, TGF-$\beta$3-98-10, TGF-$\beta$-1-rwk-5, TGF-$\beta$-3-rwk-2, TGF-$\beta$-1-rwk-5, TGF-$\beta$-3-rwk-9, TGF-$\beta$-3-rwk-23, TGF-$\beta$1-3, TGF-$\beta$1-10.

Thus oligonucleotides which are effective against expression of at least two of TGF-$\beta_1$, TGF-$\beta_2$ and/or TGF-$\beta_3$ are also part of the invention.

These findings were also surprising in view of the fact that sequence comparison between the mRNAs of TGF-$\beta_2$, TGF-$\beta_1$, and TGF-$\beta_3$ showed that not a single sequence of 20 bases in length could be found that would be identical within the three different mRNAs. Even if such a hypothetical sequence had really existed, inhibition of the three mRNAs by such a hypothetical consensus sequence would have been extremely unlikely, since it is well known in the art that only a small minority of antisense sequences complementary to a certain mRNA actually exert a so-called antisense effect, i.e. inhibit expression of the respective protein.

Endothelial synthesis of monocyte chemotactic protein-1 (MCP-1) has been implicated in the regulation of monocyte recruitment for extravascular pools both under physiological and inflammatory conditions.

MCP-1 antisense oligonucleotides were able to modulate monocyte infiltration and were thus anti-inflammatoric.

These antisense-oligonucleotides are useful for the treatment of inflammatory diseases e.g. asthma, morbus crohn, collitis ulcerosa, diabetes, glomerulonephritis, acute respiratory distress syndrome and artherosclerotic plaque formation.

In a preferred embodiment of the invention the oligonucleotides and/or ribozymes and/or nucleic acids have modifications at the bases, the sugars and/or the phosphate moieties of the oligonucleotides.

In a further preferred embodiment of the invention the oligonucleotides and/or ribozymes and/or nucleic acids have modifications wherein the modifications are phosphorothioate (S-ODN) internucleotide linkages and/or methylphosphonate internucleotide linkages and/or phosphoramidate linkages and/or peptide linkages and/or 2'-O-derivatives, such as 2'-O-methyl or 2'-O-methoxyethoxy modifications of the sugar and/or modifications of the bases.

In a further preferred embodiment of the invention the oligonucleotides and/or ribozymes and/or nucleic acids are coupled to or mixed with folic acid, hormones, steroid hormones such as oestrogene, progesterone, corticosteroids, mineral corticoids, peptides, proteoglycans, glycolipids, phospholipids, polyethylene imine or other poly cations and derivatives therefrom.

Furthermore, the present invention provides a method of treating hyperproliferative diseases, neoplasms or infectious diseases by administering a medicament of the invention to patients in need thereof. The method is especially useful for the treatment of leukemia, non-hodgkin lymphoma, hodgkin lymphoma, bronchial carcinoma, esophageal carcinoma, colorectal carcinoma, gastric carcinomas, intestinal tumors, hepatic tumors, gall bladder and gallduct carcinomas, pancreatic carcinoma, anal carcinoma, breast cancer, ovarian carcinoma, cervial carcinoma, endometrium carcinoma, prostatic carcinoma, bladder carcinoma, malignant melanoma, brain tumors, and sarcomas.

The necessary doses of the medicament of the present invention depend on the disease and the severity of the disease. Whereas higher levels are more effective, they often have a higher degree of side effects. Suitable doses are selected to obtain concentrations of the oligonucleotides in the range of 0.1 to 10 µmol/l and concentrations of the cytokines in the range of 10 to 1.000 U/ml in the patient blood.

In a preferred embodiment of the invention the inhibitor of the effect of a substance negatively effecting an immune response is applied locally to a tumor or other pathologically affected site or organ and the stimulator positively effecting an immune response is applied systemically (e.g. i.v. or s.c. or orally).

In another preferred embodiment of the invention the inhibitor of the effect of a substance negatively effecting an immune response is applied systemically (e.g. i.v or s.c. or orally) to the tumor and the stimulator positively effecting an immune response is applied locally to a tumor or other pathologically affected site or organ. In another preferred embodiment of the invention the inhibitor of the effect of a substance negatively effecting an immune response is applied systemically (e.g. i.v. or s.c. or orally) to the tumor and the stimulator positively effecting an immune response is applied systemically (e.g. i.v. or s.c. or orally).

In another preferred embodiment of the invention the inhibitor of the effect of a substance negatively effecting an immune response is applied locally to a tumor or other pathologically affected site or organ and the stimulator positively effecting an immune response is applied locally to a tumor or other pathologically affected site or organ.

FIG. 1 shows oligonucleotides useful in the present invention.

FIG. 6A shows dendritic cells generated from PBMC (% of control). Cytokines: GM-CSF (400 U/ml)+IL-4 (300 U/ml).

FIG. 6B shows lysis of tumor-cells: Effects of 5 μM VEGF-Antisense-Oligos on LAK-Cytotoxicty. Ration of tumor-cells/DC/PBMC was 1:5:20.

FIG. 7A shows effects of oligonucleotides (f.c. 5 μM) on TGF-β1 secretion in PBMC in 10% FCS RPMI 1640 medium (3 day incubation with oligonucleotides).

FIG. 7B shows effects of oligonucleotides (f.c. 5 μM) on TGF-β2 secretion in tumor cells in 10% FCS RPMI 1640 medium (3 day incubation with oligonucleotides).

EXAMPLES

Preparation of PBMC and Tumor Cells

Peripheral blood mononuclear cells (PBMC) were isolated from venous blood of healthy donors by standard Ficoll-Hypaque gradient centrifugation. Briefly, heparinized blood was mixed with equal volumes of complete medium (CM: RMPI 1640 medium supplemented with 10% (v/v) fetal calf serum and 1 mM L-Glutamine) and layered onto a Ficoll-Hypaque (Pharmacia, Uppsala, Sweden) gradient. After centrifugation at 400 g for 30 min at room temperature, PBMCs banded at the plasma-Ficoll interface were recovered, washed tree times and resuspended in complete medium. Cell viability, as determined by Trypan blue exclusion, was greater than 97%.

Human glioma cell lines were established from tumor specimens of patients with anaplastic astrocytoma (WHO Grad III) or from glioblastoma (WHO Grad IV).

Measurement of Cell Proliferation

For PBMC-proliferation assays (3H-thymidine incorporation and cell counting), freshly isolated PBMCs were cultured for 72 h in 96-well round-bottom plates (Nunc, Copenhagen, Denmark) at a final concentration (f.c.) of $10^5$ cells/well (100 μl CM). For cell number determination the cells were counted by hemacytometer. Cell viability was determined by trypan blue staining. Treated and untreated cells showed 95-100% viability after 72 h in vitro growth (with or without S-ODN).

For the tumor proliferation experiments $10^4$/100 μL glioma cells were seeded into 96-well flat-bottom plates (Nunc, Denmark) and incubated with cytokines and/or oligonucleotides. The DNA synthesis rate was measured, by a standard 3H-thymidine incorporation assay and determination of cell number was performed as described above.

Quantification of TGF-β1 Protein in Culture Supernatants by Enzyme-Linked Immunosorbent Assay (ELISA)

The culture medium was harvested after 3 days, cleared of cellular components by centrifugation, filtered and stored at −70° C. until processed further. TGF-β1 and TGF-β2 concentrations were measured after acidification of supernatants by TGF-β1 and TGF-β2 ELISA (R&D Systems, Minneapolis, USA) in duplicates, as recommended by the manufacturer.

FIGS. 1-4 and 7 show the effect of oligonucleotides on the TGF-β secretion in cells. The concentration of the TGF-β is reported as an optical density. The higher the optical density the higher is the concentration of the TGF-β.

FIGS. 1A and 1B shows the effect of the oligonucleotides on the TGF-β secretion. Control oligos (GAA GGA ATT ACC ACT TTC) have no effects whereas the oligonucleotides shown in the figures reduce the secretion of TGF-β. The oligos in FIG. 1 are more effective against TGF-β1.

Figure 2:
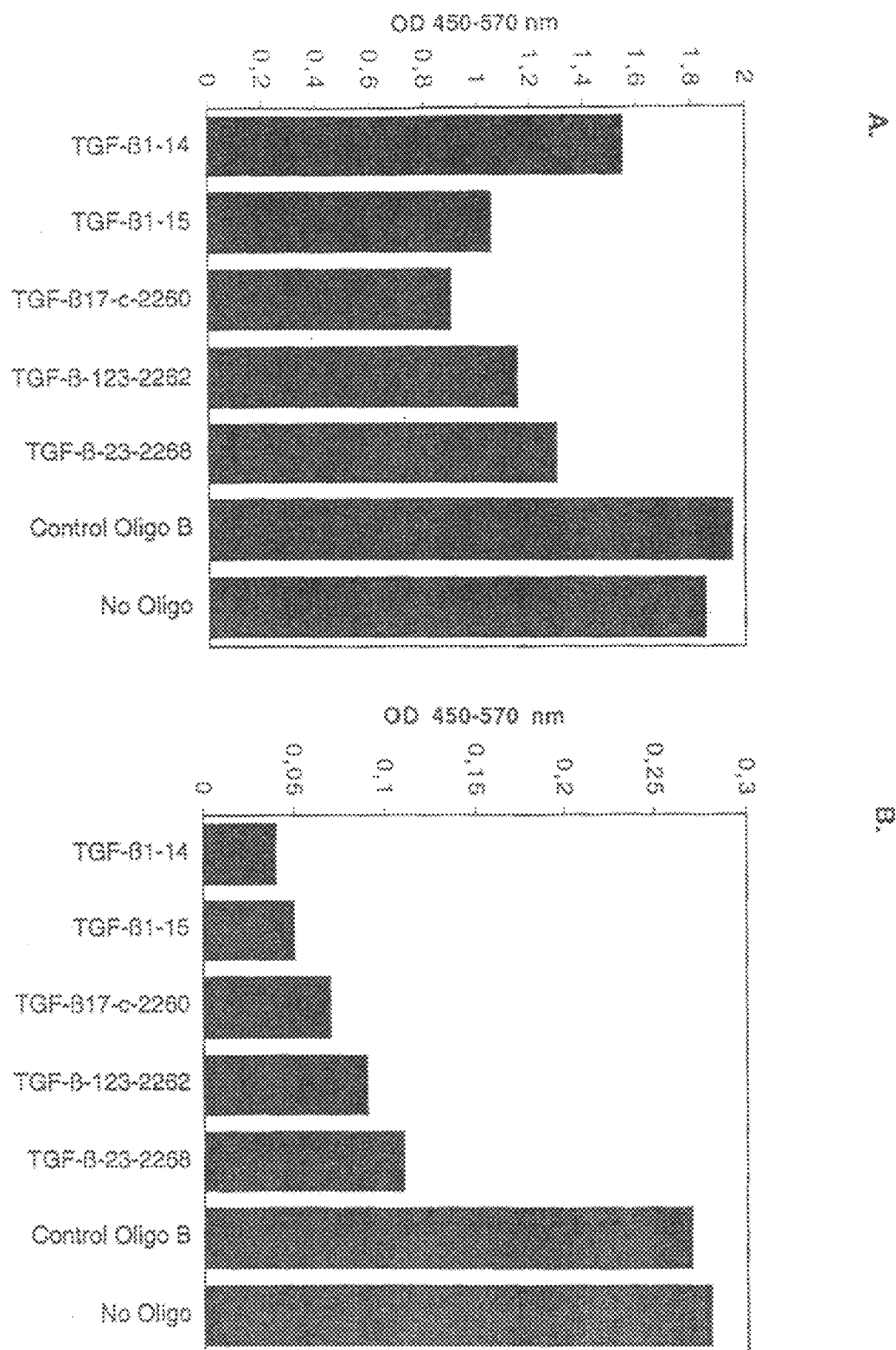
FIG. 2A shows effects of oligonucleotides (f.c. 5 μM) on TGF-β2 secretion in glioma cells in 10% MEM Dulbecco medium (3 day incubation with oligonucleotides).
FIG. 2B shows effects of oligonucleotides (f.c. 5 μM) on TGF-β1 secretion in PBMC in 10% FCS RPMI 1640 medium (3 day incubation with oligonucleotides).

FIG. 2 shows further oligos and their effects on TGF-β secretion. TGF-β-14 is especially effective against the secretion of TGF-β1 and -β2.

Figure 3:
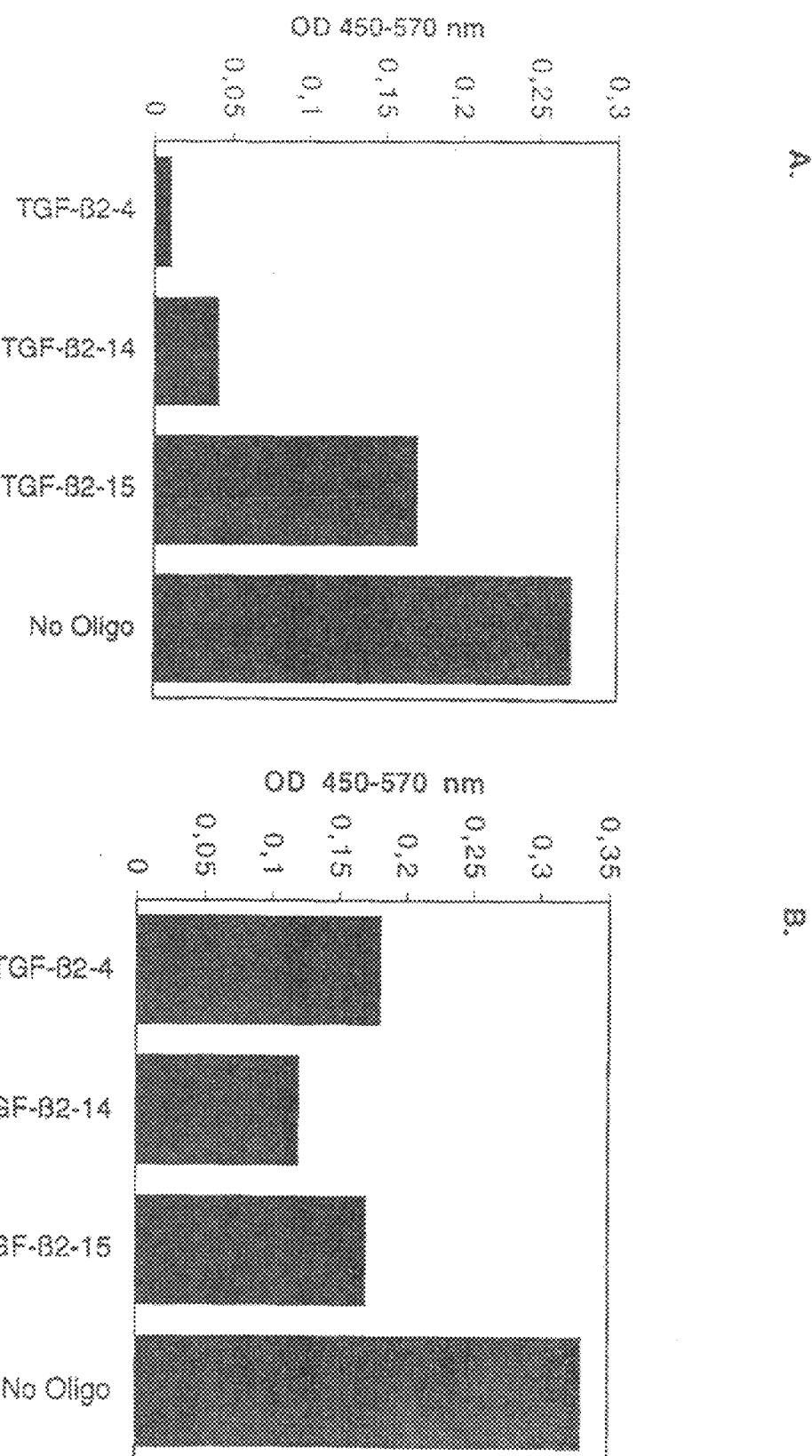
FIG. 3A shows effects of oligonucleotides (f.c. 5 μM) on TGF-β1 secretion in PBMC in 10% FCS RPMI 1640 medium (3 day incubation with oligonucleotides).
FIG. 3B shows effects of oligonucleotides (f.c. 5 μM) on TGF-β2 secretion in glioma cells in 10% FCS RPMI 1640 medium (3 day incubation with oligonucleotides).
Figure 4:
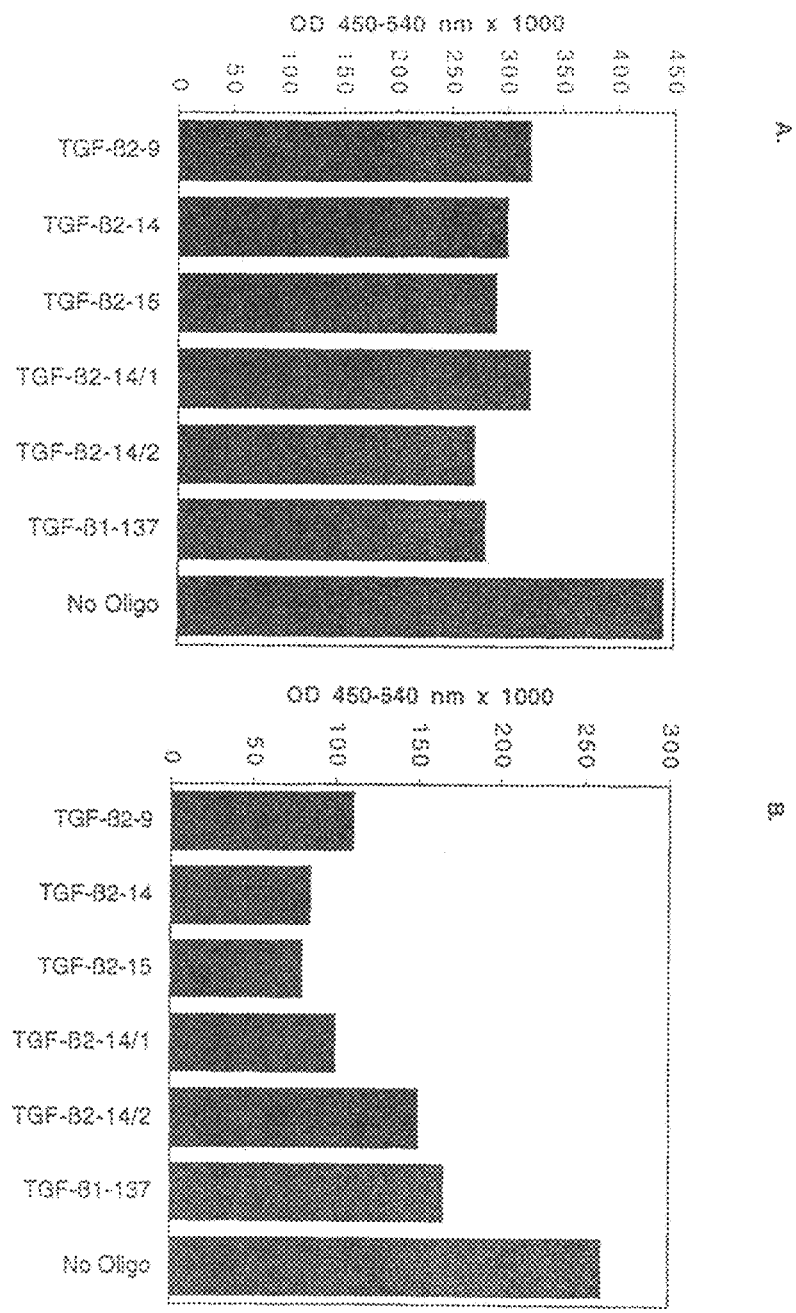
FIG. 4A shows TGF-β1 concentration (ELISA) in glioma cells (3 day incubation with oligonucleotides).
FIG. 4B shows TGF-β2 concentration (ELISA) in glioma cells (3 day incubation with oligonucleotides).
Figure 5:
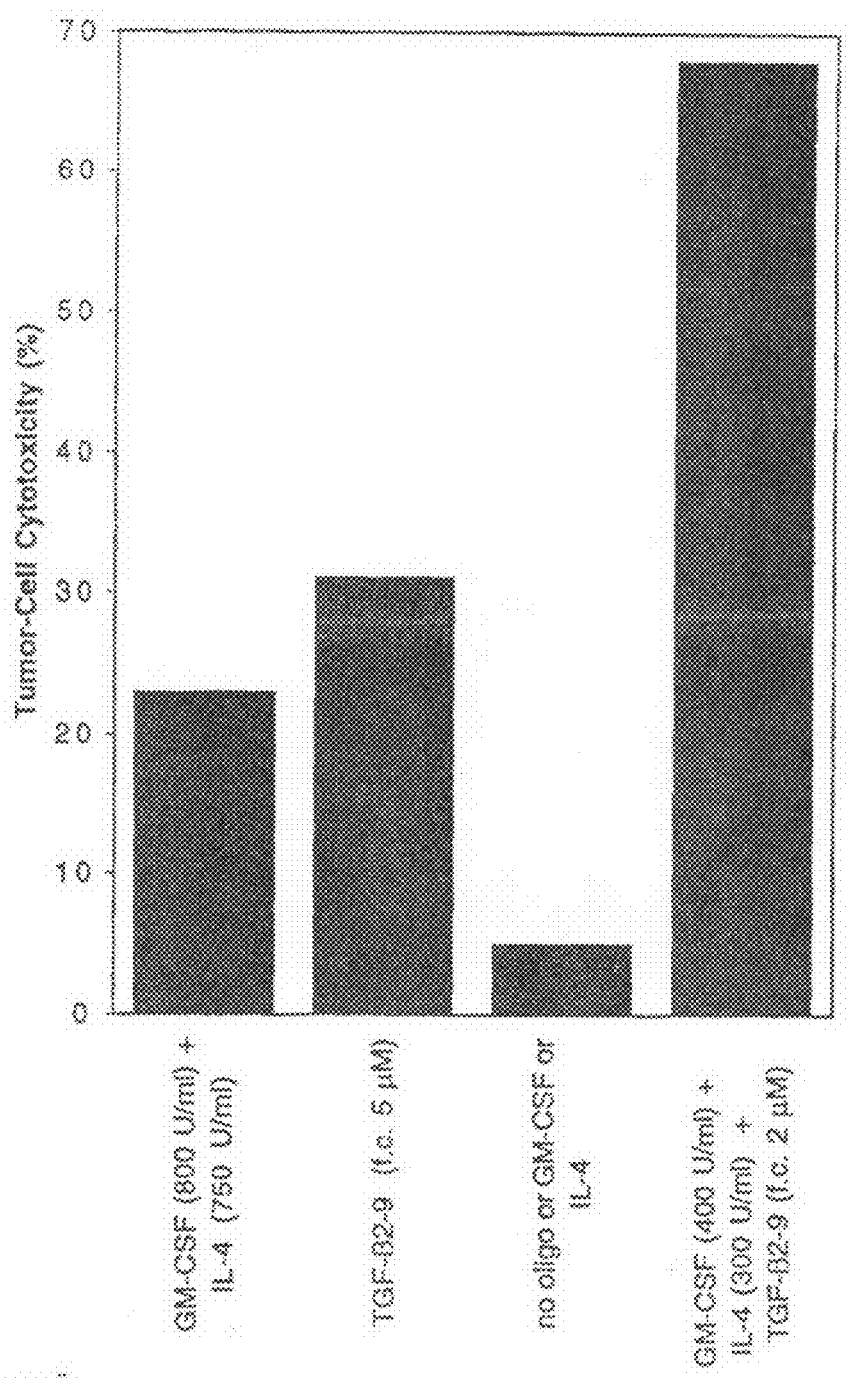
FIG. 5 shows lysis of tumor-cells: LAK-Cytotoxicty, Ratio of glioma-cells/PBMC: 1:20.

FIG. 3 shows further oligonucleotides being effective against secretion of TGF-β1 and -β2. These oligonucleotides are more effective against TGF-β2 but are also effective against TGF-β1.

Figure 8:
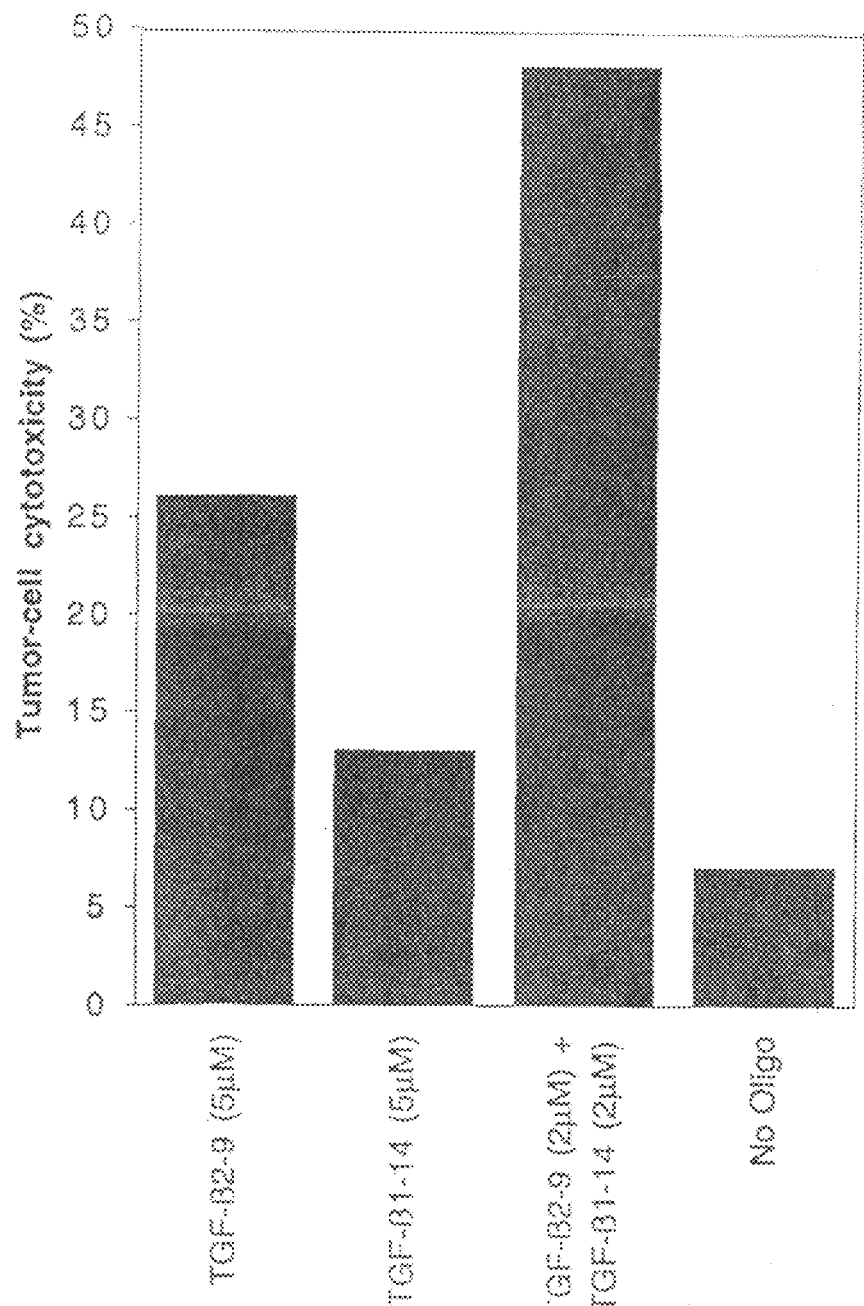
FIG. 8 shows lysis of tumor-cells: Effects of oligonucleotides on LAK-Cytotoxicty. Ration of tumor-cells/PBMC was 1:20.

FIG. 8 shows a supra additive effect on tumor cell cytotoxicity by a combination of 2 μM each of a TGF-β1 and TGF-β2 antisense oligonucleotide compared to a single 5 μM dose of either oligonucleotide.

CARE-LASS (Calcein-Release-Assay) to Measure Cytotoxic PBMC Activity

A standard calcein-release-assay (CARE-LASS assay) to determine cytotoxic activity of PBMC was employed as described by Lichtenfels, R., Biddison, W. E., Schulz, H., Vogt, A. B. and R. Martin. CARE-LASS (calcein-release assay), an improved fluorescence-based test system to measure cytotoxic lymphocyte activity. J. Immunol. Meth., 172: 227-239, 1994.

Target and Effector Cells

At the day of the assay malignant glioma were harvested, washed twice in 5% FCS/PBS and incubated with Calcein-AM (Molecular Probes, USA) for 30 min in 37° C. Labeled target cells were washed twice in 5% FCS/PBS, adjusted to 100 000/ml, and plated into 96-well U-shaped microtiter plates (Nunc, Dennmark) at the final volumen of 100 uL/well.

PBMC were washed with 5% FCS/PBS and adjusted to final concentration of 1-10 Mio cells/ml.

Cells were treated with cytokines and oligodeoxynucleotides as described in the individual experiments.

Assay

To measure CTL activity effector cells were plated into 96-well U-shape microtiter plates at Target:Effector Ratios of 1:10-1:100. To measure spontaneous release and total release of calcein, wells were preloaded with 200 uL 5% FCS/PBS or 200 uL lysis buffer (50 mM sodium-borate, 0.1% Triton, pH 9.0) respectively. After incubating the plate for 4 h at 37° C. in an incubator, 100 uL of supematans were transferred into new wells and measured employing an automated fluorescence scanner (Titertek Fluoroskan II, Germany). Both for excitation and for emission, filter settings 2 were chosen (ex 2-485 nm, em 2-538 nm). The percent of cytotoxicity was determined from the following equation:

$$\frac{F/CTL \text{ asssay} - F \text{ spontaneous release}}{F \text{ total lysis} - F \text{ spontanous release}} \times 100 = \% \text{ cytotoxicity}$$

In one set of experiments, glioma cells, denritic cells (DC) and PBMC were co-cultured. In these experiments DC were generated from PBMC using the cytokines GM-CSF and IL4. Cells were further treated with antisense VEGF-oligonucleotides according to the invention or with no oligonucleotides as control experiments. Tumor cells were also treated with the cytokines GM-CSF and IL4 with or without oligonucleotides.

PBMC were only treated with oligonucleotides according to the invention, but not with the cytokines GM-CSF and IL4. oligos were used at a concentration of 5 µM unless indicated otherwise in the descriptions in the figures.

The CARE-LASS (calcein-release-assay) was used to measure cytotoxic PBMC activity.

In one set of experiments glioma cells and PBMC were treated either with a single oligonucleotide or with a combination of oligonucleotides. The single oligonucleotides were given at 5 µM concentration. In the combination experiment, each oligonucleotide was given at 2 µM concentration. Both, PBMC and tumor cells were incubated separately with the oligonucleotide(s) for 72 h.

The CARE-LASS (calcein-release-assay) was used to measure cytotoxic PBMC activity.

The invention claimed is:

1. A composition comprising
   a) an oligonucleotide having a sequence according to SEQ ID NO: 9, unmodified or having one or more modifications selected from the group consisting of phosphorothioate internucleotide linkages, methylphosphonate internucleotide linkages, phosphoramidite linkages, peptide linkages, 2'-O-modified sugar, and modified bases, which oligonucleotide reduces the expression of transforming growth factor (TGF)-$\beta_1$, TGF-$\beta_2$, and TGF-$\beta_3$, in combination with
   b) at least one stimulator positively effecting an immune response by enhancing proliferation or function of immune cells and selected from the group consisting of Granulocyte Macrophage Colony Stimulating Factor (GM-CSF), Stem Cell Factor (SCF), Colony Stimulating Factor (CSF), Interferon (IFN), FMS-Related Tyrosine Kinase 3 Ligand (FLT-3-ligand), interleukin-4, interleukin-12, and interleukin 18.

2. The composition according to claim 1, wherein the at least one stimulator is two or more stimulators.

3. The composition according to claim 1, wherein the sequence according to SEQ ID NO: 9 is unmodified.

4. The composition according to claim 1, wherein the sequence according to SEQ ID NO: 9 has one or more modifications selected from the group consisting of phosphorothioate internucleotide linkages, methylphosphonate internucleotide linkages, phosphoramidite linkages, peptide linkages, 2'-O-modified sugar, and modified bases.

5. The composition according to claim 2, wherein the sequence according to SEQ ID NO: 9 is unmodified.

6. The composition according to claim 2, wherein the sequence according to SEQ ID NO: 9 has one or more modifications selected from the group consisting of phosphorothioate internucleotide linkages, methylphosphonate internucleotide linkages, phosphoramidite linkages, peptide linkages, 2'-O-modified sugar, and modified bases.

* * * * *

SEQUENCE LISTING

```
<160> NUMBER OF SEQ ID NOS: 213

<210> SEQ ID NO 1
<211> LENGTH: 14
<212> TYPE: DNA
<213> ORGANISM: Homo sapiens

<400> SEQUENCE: 1
cacacagtag tgca                                                          14

<210> SEQ ID NO 2
<211> LENGTH: 14
<212> TYPE: DNA
<213> ORGANISM: Homo sapiens

<400> SEQUENCE: 2
gcacacagta gtgc                                                          14

<210> SEQ ID NO 3
<211> LENGTH: 17
<212> TYPE: DNA
<213> ORGANISM: Homo sapiens

<400> SEQUENCE: 3
gcttgctcag gatctgc                                                       17

<210> SEQ ID NO 4
<211> LENGTH: 14
<212> TYPE: DNA
<213> ORGANISM: Homo sapiens

<400> SEQUENCE: 4
tactcttcgt cgct                                                          14

<210> SEQ ID NO 5
<211> LENGTH: 14
<212> TYPE: DNA
<213> ORGANISM: Homo sapiens

<400> SEQUENCE: 5
cttggcgtag tact                                                          14

<210> SEQ ID NO 6
<211> LENGTH: 14
<212> TYPE: DNA
<213> ORGANISM: Homo sapiens
```

```
<400> SEQUENCE: 6
gtaaacctcc ttgg                                                      14

<210> SEQ ID NO 7
<211> LENGTH: 19
<212> TYPE: DNA
<213> ORGANISM: Homo sapiens

<400> SEQUENCE: 7
gtctattttg taaacctcc                                                 19

<210> SEQ ID NO 8
<211> LENGTH: 20
<212> TYPE: DNA
<213> ORGANISM: Homo sapiens

<400> SEQUENCE: 8
gcatgtctat tttgtaaacc                                                20

<210> SEQ ID NO 9
<211> LENGTH: 18
<212> TYPE: DNA
<213> ORGANISM: Homo sapiens

<400> SEQUENCE: 9
cggcatgtct attttgta                                                  18

<210> SEQ ID NO 10
<211> LENGTH: 14
<212> TYPE: DNA
<213> ORGANISM: Homo sapiens

<400> SEQUENCE: 10
ggcatcaagg tacc                                                      14

<210> SEQ ID NO 11
<211> LENGTH: 14
<212> TYPE: DNA
<213> ORGANISM: Homo sapiens

<400> SEQUENCE: 11
ctgtagaaag tggg                                                      14

<210> SEQ ID NO 12
<211> LENGTH: 18
<212> TYPE: DNA
<213> ORGANISM: Homo sapiens

<400> SEQUENCE: 12
acaattctga agtagggt                                                  18

<210> SEQ ID NO 13
<211> LENGTH: 18
<212> TYPE: DNA
<213> ORGANISM: Homo sapiens

<400> SEQUENCE: 13
tcaccaaatt ggaagcat                                                  18

<210> SEQ ID NO 14
<211> LENGTH: 20
<212> TYPE: DNA
<213> ORGANISM: Homo sapiens
```

```
<400> SEQUENCE: 14
gctttcacca aattggaagc                                                  20

<210> SEQ ID NO 15
<211> LENGTH: 14
<212> TYPE: DNA
<213> ORGANISM: Homo sapiens

<400> SEQUENCE: 15
ctggcttttg ggtt                                                        14

<210> SEQ ID NO 16
<211> LENGTH: 18
<212> TYPE: DNA
<213> ORGANISM: Homo sapiens

<400> SEQUENCE: 16
tctgatatag ctcaatcc                                                    18

<210> SEQ ID NO 17
<211> LENGTH: 18
<212> TYPE: DNA
<213> ORGANISM: Homo sapiens

<400> SEQUENCE: 17
tcctagtgga ctttatag                                                    18

<210> SEQ ID NO 18
<211> LENGTH: 16
<212> TYPE: DNA
<213> ORGANISM: Homo sapiens

<400> SEQUENCE: 18
tttttcctag tggact                                                      16

<210> SEQ ID NO 19
<211> LENGTH: 19
<212> TYPE: DNA
<213> ORGANISM: Homo sapiens

<400> SEQUENCE: 19
caattatcct gcacatttc                                                   19

<210> SEQ ID NO 20
<211> LENGTH: 16
<212> TYPE: DNA
<213> ORGANISM: Homo sapiens

<400> SEQUENCE: 20
gcaattatcc tgcaca                                                      16

<210> SEQ ID NO 21
<211> LENGTH: 16
<212> TYPE: DNA
<213> ORGANISM: Homo sapiens

<400> SEQUENCE: 21
gcagcaatta tcctgc                                                      16

<210> SEQ ID NO 22
<211> LENGTH: 14
<212> TYPE: DNA
<213> ORGANISM: Homo sapiens
```

-continued

```
<400> SEQUENCE: 22
tggcattgta ccct                                              14

<210> SEQ ID NO 23
<211> LENGTH: 14
<212> TYPE: DNA
<213> ORGANISM: Homo sapiens

<400> SEQUENCE: 23
tgtgctgagt gtct                                              14

<210> SEQ ID NO 24
<211> LENGTH: 16
<212> TYPE: DNA
<213> ORGANISM: Homo sapiens

<400> SEQUENCE: 24
cctgctgtgc tgagtg                                            16

<210> SEQ ID NO 25
<211> LENGTH: 14
<212> TYPE: DNA
<213> ORGANISM: Homo sapiens

<400> SEQUENCE: 25
cttgggtgtt ttgc                                              14

<210> SEQ ID NO 26
<211> LENGTH: 18
<212> TYPE: DNA
<213> ORGANISM: Homo sapiens

<400> SEQUENCE: 26
tttagctgca tttgcaag                                          18

<210> SEQ ID NO 27
<211> LENGTH: 14
<212> TYPE: DNA
<213> ORGANISM: Homo sapiens

<400> SEQUENCE: 27 gccactttc caag                                               14

<210> SEQ ID NO 28
<211> LENGTH: 18
<212> TYPE: DNA
<213> ORGANISM: Homo sapiens

<400> SEQUENCE: 28
ctttcaccaa attggaag                                          18

<210> SEQ ID NO 29
<211> LENGTH: 15
<212> TYPE: DNA
<213> ORGANISM: Homo sapiens

<400> SEQUENCE: 29
caccaaattg gaagc                                             15

<210> SEQ ID NO 30
<211> LENGTH: 16
<212> TYPE: DNA
<213> ORGANISM: Homo sapiens
```

```
<400> SEQUENCE: 30
tcaccaaatt ggaagc                                                    16

<210> SEQ ID NO 31
<211> LENGTH: 14
<212> TYPE: DNA
<213> ORGANISM: Homo sapiens

<400> SEQUENCE: 31
ctctggcttt tggg                                                      14

<210> SEQ ID NO 32
<211> LENGTH: 16
<212> TYPE: DNA
<213> ORGANISM: Homo sapiens

<400> SEQUENCE: 32
cggcatgtct attttg                                                    16

<210> SEQ ID NO 33
<211> LENGTH: 14
<212> TYPE: DNA
<213> ORGANISM: Homo sapiens

<400> SEQUENCE: 33
cgatagtctt gcag                                                      14

<210> SEQ ID NO 34
<211> LENGTH: 14
<212> TYPE: DNA
<213> ORGANISM: Homo sapiens

<400> SEQUENCE: 34
gtcgatagtc ttgc                                                      14

<210> SEQ ID NO 35
<211> LENGTH: 14
<212> TYPE: DNA
<213> ORGANISM: Homo sapiens

<400> SEQUENCE: 35
cttggacagg atct                                                      14

<210> SEQ ID NO 36
<211> LENGTH: 14
<212> TYPE: DNA
<213> ORGANISM: Homo sapiens

<400> SEQUENCE: 36
ccaggaattg ttgc                                                      14

<210> SEQ ID NO 37
<211> LENGTH: 14
<212> TYPE: DNA
<213> ORGANISM: Homo sapiens

<400> SEQUENCE: 37
cctcaatttc ccct                                                      14

<210> SEQ ID NO 38
<211> LENGTH: 14
<212> TYPE: DNA
<213> ORGANISM: Homo sapiens
```

```
<400> SEQUENCE: 38
gatgtccact tgca                                                  14

<210> SEQ ID NO 39
<211> LENGTH: 14
<212> TYPE: DNA
<213> ORGANISM: Homo sapiens

<400> SEQUENCE: 39
ctccaaatgt aggg                                                  14

<210> SEQ ID NO 40
<211> LENGTH: 14
<212> TYPE: DNA
<213> ORGANISM: Homo sapiens

<400> SEQUENCE: 40
accttgctgt actg                                                  14

<210> SEQ ID NO 41
<211> LENGTH: 14
<212> TYPE: DNA
<213> ORGANISM: Homo sapiens

<400> SEQUENCE: 41
gtagtacacg atgg                                                  14

<210> SEQ ID NO 42
<211> LENGTH: 14
<212> TYPE: DNA
<213> ORGANISM: Homo sapiens

<400> SEQUENCE: 42
cacgtagtac acga                                                  14

<210> SEQ ID NO 43
<211> LENGTH: 14
<212> TYPE: DNA
<213> ORGANISM: Homo sapiens

<400> SEQUENCE: 43
catgttggac agct                                                  14

<210> SEQ ID NO 44
<211> LENGTH: 14
<212> TYPE: DNA
<213> ORGANISM: Homo sapiens

<400> SEQUENCE: 44
gcacgatcat gttg                                                  14

<210> SEQ ID NO 45
<211> LENGTH: 16
<212> TYPE: DNA
<213> ORGANISM: Homo sapiens

<400> SEQUENCE: 45
tgtactctgc ttgaac                                                16

<210> SEQ ID NO 46
<211> LENGTH: 18
<212> TYPE: DNA
<213> ORGANISM: Homo sapiens
```

```
<400> SEQUENCE: 46
ctgatgtgtt gaagaaca                                                 18

<210> SEQ ID NO 47
<211> LENGTH: 16
<212> TYPE: DNA
<213> ORGANISM: Homo sapiens

<400> SEQUENCE: 47
ctctgatgtg ttgaag                                                   16

<210> SEQ ID NO 48
<211> LENGTH: 16
<212> TYPE: DNA
<213> ORGANISM: Homo sapiens

<400> SEQUENCE: 48
ggaagtcaat gtacag                                                   16

<210> SEQ ID NO 49
<211> LENGTH: 18
<212> TYPE: DNA
<213> ORGANISM: Homo sapiens

<400> SEQUENCE: 49
catgtcgata gtcttgca                                                 18

<210> SEQ ID NO 50
<211> LENGTH: 18
<212> TYPE: DNA
<213> ORGANISM: Homo sapiens

<400> SEQUENCE: 50
agctgaagca atagttgg                                                 18

<210> SEQ ID NO 51
<211> LENGTH: 18
<212> TYPE: DNA
<213> ORGANISM: Homo sapiens

<400> SEQUENCE: 51
gtcatagatt tcgttgtg                                                 18

<210> SEQ ID NO 52
<211> LENGTH: 18
<212> TYPE: DNA
<213> ORGANISM: Homo sapiens

<400> SEQUENCE: 52
ctccactttt aacttgag                                                 18

<210> SEQ ID NO 53
<211> LENGTH: 18
<212> TYPE: DNA
<213> ORGANISM: Homo sapiens

<400> SEQUENCE: 53
tgctgtattt ctggtaca                                                 18

<210> SEQ ID NO 54
<211> LENGTH: 14
<212> TYPE: DNA
<213> ORGANISM: Homo sapiens
```

```
<400> SEQUENCE: 54
cgatagtctt gcag                                                      14

<210> SEQ ID NO 55
<211> LENGTH: 18
<212> TYPE: DNA
<213> ORGANISM: Homo sapiens

<400> SEQUENCE: 55
tcctcttcga ctgctctc                                                  18

<210> SEQ ID NO 56
<211> LENGTH: 20
<212> TYPE: DNA
<213> ORGANISM: Homo sapiens

<400> SEQUENCE: 56
cgaaggttaa accactttcg                                                20

<210> SEQ ID NO 57
<211> LENGTH: 16
<212> TYPE: DNA
<213> ORGANISM: Homo sapiens

<400> SEQUENCE: 57
gtgagtcgtg tcgtcc                                                    16

<210> SEQ ID NO 58
<211> LENGTH: 14
<212> TYPE: DNA
<213> ORGANISM: Homo sapiens

<400> SEQUENCE: 58
catcgttgtc gtcg                                                      14

<210> SEQ ID NO 59
<211> LENGTH: 14
<212> TYPE: DNA
<213> ORGANISM: Homo sapiens

<400> SEQUENCE: 59
cgcttcttcc gccg                                                      14

<210> SEQ ID NO 60
<211> LENGTH: 17
<212> TYPE: DNA
<213> ORGANISM: Homo sapiens

<400> SEQUENCE: 60
cgaaggagag ccattcg                                                   17

<210> SEQ ID NO 61
<211> LENGTH: 10
<212> TYPE: DNA
<213> ORGANISM: Homo sapiens

<400> SEQUENCE: 61
cgatgtagcg                                                           10

<210> SEQ ID NO 62
<211> LENGTH: 10
<212> TYPE: DNA
<213> ORGANISM: Homo sapiens
```

```
<400> SEQUENCE: 62
cgtcaaatcg                                                            10

<210> SEQ ID NO 63
<211> LENGTH: 17
<212> TYPE: DNA
<213> ORGANISM: Homo sapiens

<400> SEQUENCE: 63
cgtagtactc ttcgtcg                                                    17

<210> SEQ ID NO 64
<211> LENGTH: 14
<212> TYPE: DNA
<213> ORGANISM: Homo sapiens

<400> SEQUENCE: 64
cgcgctcgca ggcg                                                       14

<210> SEQ ID NO 65
<211> LENGTH: 18
<212> TYPE: DNA
<213> ORGANISM: Homo sapiens

<400> SEQUENCE: 65
cggccgccct ccggctcg                                                   18

<210> SEQ ID NO 66
<211> LENGTH: 14
<212> TYPE: DNA
<213> ORGANISM: Homo sapiens

<400> SEQUENCE: 66
cgcggatcgc ctcg                                                       14

<210> SEQ ID NO 67
<211> LENGTH: 15
<212> TYPE: DNA
<213> ORGANISM: Homo sapiens

<400> SEQUENCE: 67
gagcgcgacc gtgac                                                      15

<210> SEQ ID NO 68
<211> LENGTH: 17
<212> TYPE: DNA
<213> ORGANISM: Homo sapiens

<400> SEQUENCE: 68
acctccttgg cgtagta                                                    17

<210> SEQ ID NO 69
<211> LENGTH: 20
<212> TYPE: DNA
<213> ORGANISM: Homo sapiens

<400> SEQUENCE: 69
agggcggcat gtctattttg                                                 20

<210> SEQ ID NO 70
<211> LENGTH: 18
<212> TYPE: DNA
<213> ORGANISM: Homo sapiens
```

```
<400> SEQUENCE: 70
cagaagttgg cattgtac                                                 18

<210> SEQ ID NO 71
<211> LENGTH: 22
<212> TYPE: DNA
<213> ORGANISM: Homo sapiens

<400> SEQUENCE: 71
agggcggcat gtctattttg ta                                            22

<210> SEQ ID NO 72
<211> LENGTH: 17
<212> TYPE: DNA
<213> ORGANISM: Homo sapiens

<400> SEQUENCE: 72
tgggacacgc agcaagg                                                  17

<210> SEQ ID NO 73
<211> LENGTH: 16
<212> TYPE: DNA
<213> ORGANISM: Homo sapiens

<400> SEQUENCE: 73
cgggggcggg gcgggg                                                   16

<210> SEQ ID NO 74
<211> LENGTH: 17
<212> TYPE: DNA
<213> ORGANISM: Homo sapiens

<400> SEQUENCE: 74
cggggcgggg cggggcg                                                  17

<210> SEQ ID NO 75
<211> LENGTH: 20
<212> TYPE: DNA
<213> ORGANISM: Homo sapiens

<400> SEQUENCE: 75
cggcgccgcc gaggcgcccg                                               20

<210> SEQ ID NO 76
<211> LENGTH: 15
<212> TYPE: DNA
<213> ORGANISM: Homo sapiens

<400> SEQUENCE: 76
ccgaggtcct tgcgg                                                    15

<210> SEQ ID NO 77
<211> LENGTH: 14
<212> TYPE: DNA
<213> ORGANISM: Homo sapiens

<400> SEQUENCE: 77
cggcggtgcc ggga                                                     14

<210> SEQ ID NO 78
<211> LENGTH: 15
<212> TYPE: DNA
<213> ORGANISM: Homo sapiens
```

-continued

```
<400> SEQUENCE: 78
ctcggcggcc ggtag                                                      15

<210> SEQ ID NO 79
<211> LENGTH: 10
<212> TYPE: DNA
<213> ORGANISM: Homo sapiens

<400> SEQUENCE: 79
cgctaaggcg                                                            10

<210> SEQ ID NO 80
<211> LENGTH: 14
<212> TYPE: DNA
<213> ORGANISM: Homo sapiens

<400> SEQUENCE: 80
ccgcacaact ccgg                                                       14

<210> SEQ ID NO 81
<211> LENGTH: 12
<212> TYPE: DNA
<213> ORGANISM: Homo sapiens

<400> SEQUENCE: 81
gcgagtcgct gg                                                         12

<210> SEQ ID NO 82
<211> LENGTH: 17
<212> TYPE: DNA
<213> ORGANISM: Homo sapiens

<400> SEQUENCE: 82
cggttgctga ggtatcg                                                    17

<210> SEQ ID NO 83
<211> LENGTH: 17
<212> TYPE: DNA
<213> ORGANISM: Homo sapiens

<400> SEQUENCE: 83
ccgggagagc aacacgg                                                    17

<210> SEQ ID NO 84
<211> LENGTH: 9
<212> TYPE: DNA
<213> ORGANISM: Homo sapiens

<400> SEQUENCE: 84 cgcttctcg                                                              9

<210> SEQ ID NO 85
<211> LENGTH: 15
<212> TYPE: DNA
<213> ORGANISM: Homo sapiens

<400> SEQUENCE: 85
ccattagcac gcggg                                                      15

<210> SEQ ID NO 86
<211> LENGTH: 9
<212> TYPE: DNA
<213> ORGANISM: Homo sapiens
```

```
<400> SEQUENCE: 86 cgggctccg                                                                9

<210> SEQ ID NO 87
<211> LENGTH: 18
<212> TYPE: DNA
<213> ORGANISM: Homo sapiens

<400> SEQUENCE: 87
ccggccaccc ggtcgcgg                                                     18

<210> SEQ ID NO 88
<211> LENGTH: 14
<212> TYPE: DNA
<213> ORGANISM: Homo sapiens

<400> SEQUENCE: 88
cgagcacggc ctcg                                                         14

<210> SEQ ID NO 89
<211> LENGTH: 18
<212> TYPE: DNA
<213> ORGANISM: Homo sapiens

<400> SEQUENCE: 89
cgggcagcgg gccgggcg                                                     18

<210> SEQ ID NO 90
<211> LENGTH: 14
<212> TYPE: DNA
<213> ORGANISM: Homo sapiens

<400> SEQUENCE: 90
cgcggatggc ctcg                                                         14

<210> SEQ ID NO 91
<211> LENGTH: 13
<212> TYPE: DNA
<213> ORGANISM: Homo sapiens

<400> SEQUENCE: 91
cgatgcgctt ccg                                                          13

<210> SEQ ID NO 92
<211> LENGTH: 15
<212> TYPE: DNA
<213> ORGANISM: Homo sapiens

<400> SEQUENCE: 92
cccgcggccg gcggg                                                        15

<210> SEQ ID NO 93
<211> LENGTH: 16
<212> TYPE: DNA
<213> ORGANISM: Homo sapiens

<400> SEQUENCE: 93
cgcagcccgg agggcg                                                       16

<210> SEQ ID NO 94
<211> LENGTH: 12
<212> TYPE: DNA
<213> ORGANISM: Homo sapiens
```

```
<400> SEQUENCE: 94
cggcgccccc cg                                                     12

<210> SEQ ID NO 95
<211> LENGTH: 19
<212> TYPE: DNA
<213> ORGANISM: Homo sapiens

<400> SEQUENCE: 95
cggcactgcc gagagcgcg                                              19

<210> SEQ ID NO 96
<211> LENGTH: 17
<212> TYPE: DNA
<213> ORGANISM: Homo sapiens

<400> SEQUENCE: 96
cggggatgaa ggcggcg                                                17

<210> SEQ ID NO 97
<211> LENGTH: 17
<212> TYPE: DNA
<213> ORGANISM: Homo sapiens

<400> SEQUENCE: 97
cgggtcggcg actcccg                                                17

<210> SEQ ID NO 98
<211> LENGTH: 16
<212> TYPE: DNA
<213> ORGANISM: Homo sapiens

<400> SEQUENCE: 98
cgcctgaggg acgccg                                                 16

<210> SEQ ID NO 99
<211> LENGTH: 14
<212> TYPE: DNA
<213> ORGANISM: Homo sapiens

<400> SEQUENCE: 99
aagcgtcccc ggcg                                                   14

<210> SEQ ID NO 100
<211> LENGTH: 17
<212> TYPE: DNA
<213> ORGANISM: Homo sapiens

<400> SEQUENCE: 100
cgcggggcag cgtcgcg                                                17

<210> SEQ ID NO 101
<211> LENGTH: 14
<212> TYPE: DNA
<213> ORGANISM: Homo sapiens

<400> SEQUENCE: 101
ccccgcgcct ccgg                                                   14

<210> SEQ ID NO 102
<211> LENGTH: 13
<212> TYPE: DNA
<213> ORGANISM: Homo sapiens
```

-continued

```
<400> SEQUENCE: 102
cggcggcggc tcg                                                        13

<210> SEQ ID NO 103
<211> LENGTH: 18
<212> TYPE: DNA
<213> ORGANISM: Homo sapiens

<400> SEQUENCE: 103
cgctccgggc cgaggccg                                                   18

<210> SEQ ID NO 104
<211> LENGTH: 14
<212> TYPE: DNA
<213> ORGANISM: Homo sapiens

<400> SEQUENCE: 104
cggccccgcg ggcg                                                       14

<210> SEQ ID NO 105
<211> LENGTH: 14
<212> TYPE: DNA
<213> ORGANISM: Homo sapiens

<400> SEQUENCE: 105
cggacggggc gtcc                                                       14

<210> SEQ ID NO 106
<211> LENGTH: 15
<212> TYPE: DNA
<213> ORGANISM: Homo sapiens

<400> SEQUENCE: 106
cggccggggc cctcg                                                      15

<210> SEQ ID NO 107
<211> LENGTH: 14
<212> TYPE: DNA
<213> ORGANISM: Homo sapiens

<400> SEQUENCE: 107
tcgagcttcc ccga                                                       14

<210> SEQ ID NO 108
<211> LENGTH: 14
<212> TYPE: DNA
<213> ORGANISM: Homo sapiens

<400> SEQUENCE: 108
cccggagccg aagg                                                       14

<210> SEQ ID NO 109
<211> LENGTH: 13
<212> TYPE: DNA
<213> ORGANISM: Homo sapiens

<400> SEQUENCE: 109
cccgaggagc ggg                                                        13

<210> SEQ ID NO 110
<211> LENGTH: 14
<212> TYPE: DNA
<213> ORGANISM: Homo sapiens
```

```
<400> SEQUENCE: 110
acgcagcaag gcga                                                      14

<210> SEQ ID NO 111
<211> LENGTH: 15
<212> TYPE: DNA
<213> ORGANISM: Homo sapiens

<400> SEQUENCE: 111
cgggttgtcg agccg                                                     15

<210> SEQ ID NO 112
<211> LENGTH: 13
<212> TYPE: DNA
<213> ORGANISM: Homo sapiens

<400> SEQUENCE: 112
cggcagtgcc ccg                                                       13

<210> SEQ ID NO 113
<211> LENGTH: 14
<212> TYPE: DNA
<213> ORGANISM: Homo sapiens

<400> SEQUENCE: 113
cggaattctg ctcg                                                      14

<210> SEQ ID NO 114
<211> LENGTH: 14
<212> TYPE: DNA
<213> ORGANISM: Homo sapiens

<400> SEQUENCE: 114
ttcgttgtgc tccg                                                      14

<210> SEQ ID NO 115
<211> LENGTH: 14
<212> TYPE: DNA
<213> ORGANISM: Homo sapiens

<400> SEQUENCE: 115
attccgactc ggtg                                                      14

<210> SEQ ID NO 116
<211> LENGTH: 17
<212> TYPE: DNA
<213> ORGANISM: Homo sapiens

<400> SEQUENCE: 116
acgtgggtca tcaccgt                                                   17

<210> SEQ ID NO 117
<211> LENGTH: 10
<212> TYPE: DNA
<213> ORGANISM: Homo sapiens

<400> SEQUENCE: 117
cgaagaagcg                                                           10

<210> SEQ ID NO 118
<211> LENGTH: 14
<212> TYPE: DNA
<213> ORGANISM: Homo sapiens
```

```
<400> SEQUENCE: 118
cctaatggct tcca                                                        14

<210> SEQ ID NO 119
<211> LENGTH: 14
<212> TYPE: DNA
<213> ORGANISM: Homo sapiens

<400> SEQUENCE: 119
cggccgcggt gtgt                                                        14

<210> SEQ ID NO 120
<211> LENGTH: 17
<212> TYPE: DNA
<213> ORGANISM: Homo sapiens

<400> SEQUENCE: 120
cgggaatgct tccgccg                                                     17

<210> SEQ ID NO 121
<211> LENGTH: 17
<212> TYPE: DNA
<213> ORGANISM: Homo sapiens

<400> SEQUENCE: 121
cggctcaccg cctcggc                                                     17

<210> SEQ ID NO 122
<211> LENGTH: 14
<212> TYPE: DNA
<213> ORGANISM: Homo sapiens

<400> SEQUENCE: 122
cacgtctgcg gatc                                                        14

<210> SEQ ID NO 123
<211> LENGTH: 18
<212> TYPE: DNA
<213> ORGANISM: Homo sapiens

<400> SEQUENCE: 123
ccccgcatcg catcaggg                                                    18

<210> SEQ ID NO 124
<211> LENGTH: 14
<212> TYPE: DNA
<213> ORGANISM: Homo sapiens

<400> SEQUENCE: 124
cgccttgcaa cgcg                                                        14

<210> SEQ ID NO 125
<211> LENGTH: 14
<212> TYPE: DNA
<213> ORGANISM: Homo sapiens

<400> SEQUENCE: 125
ccgaccgggg ccgg                                                        14

<210> SEQ ID NO 126
<211> LENGTH: 14
<212> TYPE: DNA
<213> ORGANISM: Homo sapiens
```

<400> SEQUENCE: 126
gttcatggtt tcgg                                                          14

<210> SEQ ID NO 127
<211> LENGTH: 15
<212> TYPE: DNA
<213> ORGANISM: Homo sapiens

<400> SEQUENCE: 127
gcagaaagtt catgg                                                         15

<210> SEQ ID NO 128
<211> LENGTH: 14
<212> TYPE: DNA
<213> ORGANISM: Homo sapiens

<400> SEQUENCE: 128
gctgatagac atcc                                                          14

<210> SEQ ID NO 129
<211> LENGTH: 14
<212> TYPE: DNA
<213> ORGANISM: Homo sapiens

<400> SEQUENCE: 129
gcgctgatag acat                                                          14

<210> SEQ ID NO 130
<211> LENGTH: 16
<212> TYPE: DNA
<213> ORGANISM: Homo sapiens

<400> SEQUENCE: 130
gtagctgcgc tgatag                                                        16

<210> SEQ ID NO 131
<211> LENGTH: 14
<212> TYPE: DNA
<213> ORGANISM: Homo sapiens

<400> SEQUENCE: 131
ctcgatctca tcag                                                          14

<210> SEQ ID NO 132
<211> LENGTH: 17
<212> TYPE: DNA
<213> ORGANISM: Homo sapiens

<400> SEQUENCE: 132
atgtactcga tctcatc                                                       17

<210> SEQ ID NO 133
<211> LENGTH: 16
<212> TYPE: DNA
<213> ORGANISM: Homo sapiens

<400> SEQUENCE: 133
gaagatgtac tcgatc                                                        16

<210> SEQ ID NO 134
<211> LENGTH: 16
<212> TYPE: DNA
<213> ORGANISM: Homo sapiens

```
<400> SEQUENCE: 134
cttgaagatg tactcg                                                    16

<210> SEQ ID NO 135
<211> LENGTH: 14
<212> TYPE: DNA
<213> ORGANISM: Homo sapiens

<400> SEQUENCE: 135
gcatcgcatc aggg                                                      14

<210> SEQ ID NO 136
<211> LENGTH: 14
<212> TYPE: DNA
<213> ORGANISM: Homo sapiens

<400> SEQUENCE: 136
ccgcatcgca tcag                                                      14

<210> SEQ ID NO 137
<211> LENGTH: 18
<212> TYPE: DNA
<213> ORGANISM: Homo sapiens

<400> SEQUENCE: 137
catttgttgt gctgtagg                                                  18

<210> SEQ ID NO 138
<211> LENGTH: 18
<212> TYPE: DNA
<213> ORGANISM: Homo sapiens

<400> SEQUENCE: 138
ggtctgcatt cacatttg                                                  18

<210> SEQ ID NO 139
<211> LENGTH: 15
<212> TYPE: DNA
<213> ORGANISM: Homo sapiens

<400> SEQUENCE: 139
ctttggtctg cattc                                                     15

<210> SEQ ID NO 140
<211> LENGTH: 15
<212> TYPE: DNA
<213> ORGANISM: Homo sapiens

<400> SEQUENCE: 140
ctttctttgg tctgc                                                     15

<210> SEQ ID NO 141
<211> LENGTH: 17
<212> TYPE: DNA
<213> ORGANISM: Homo sapiens

<400> SEQUENCE: 141
gctctatctt tctttgg                                                   17

<210> SEQ ID NO 142
<211> LENGTH: 17
<212> TYPE: DNA
<213> ORGANISM: Homo sapiens
```

```
<400> SEQUENCE: 142
gtcttgctct atctttc                                                  17

<210> SEQ ID NO 143
<211> LENGTH: 16
<212> TYPE: DNA
<213> ORGANISM: Homo sapiens

<400> SEQUENCE: 143
cttgtcttgc tctatc                                                   16

<210> SEQ ID NO 144
<211> LENGTH: 18
<212> TYPE: DNA
<213> ORGANISM: Homo sapiens

<400> SEQUENCE: 144
catctgcaag tacgttcg                                                 18

<210> SEQ ID NO 145
<211> LENGTH: 18
<212> TYPE: DNA
<213> ORGANISM: Homo sapiens

<400> SEQUENCE: 145
cacatctgca agtacgtt                                                 18

<210> SEQ ID NO 146
<211> LENGTH: 18
<212> TYPE: DNA
<213> ORGANISM: Homo sapiens

<400> SEQUENCE: 146
gtcacatctg caagtacg                                                 18

<210> SEQ ID NO 147
<211> LENGTH: 14
<212> TYPE: DNA
<213> ORGANISM: Homo sapiens

<400> SEQUENCE: 147
catctgcaag tacg                                                     14

<210> SEQ ID NO 148
<211> LENGTH: 15
<212> TYPE: DNA
<213> ORGANISM: Homo sapiens

<400> SEQUENCE: 148
cacatctgca agtac                                                    15

<210> SEQ ID NO 149
<211> LENGTH: 14
<212> TYPE: DNA
<213> ORGANISM: Homo sapiens

<400> SEQUENCE: 149
gtcacatctg caag                                                     14

<210> SEQ ID NO 150
<211> LENGTH: 14
<212> TYPE: DNA
<213> ORGANISM: Homo sapiens
```

```
<400> SEQUENCE: 150
cttgtcacat ctgc                                                    14

<210> SEQ ID NO 151
<211> LENGTH: 16
<212> TYPE: DNA
<213> ORGANISM: Homo sapiens

<400> SEQUENCE: 151
ggcttgtcac atctgc                                                  16

<210> SEQ ID NO 152
<211> LENGTH: 16
<212> TYPE: DNA
<213> ORGANISM: Homo sapiens

<400> SEQUENCE: 152
ctcggcttgt cacatc                                                  16

<210> SEQ ID NO 153
<211> LENGTH: 14
<212> TYPE: DNA
<213> ORGANISM: Homo sapiens

<400> SEQUENCE: 153
ctccttcctc ctgc                                                    14

<210> SEQ ID NO 154
<211> LENGTH: 18
<212> TYPE: DNA
<213> ORGANISM: Homo sapiens

<400> SEQUENCE: 154
gcttgaagat gtacctcg                                                18

<210> SEQ ID NO 155
<211> LENGTH: 15
<212> TYPE: DNA
<213> ORGANISM: Homo sapiens

<400> SEQUENCE: 155
cgttgctctc cgacg                                                   15

<210> SEQ ID NO 156
<211> LENGTH: 15
<212> TYPE: DNA
<213> ORGANISM: Homo sapiens

<400> SEQUENCE: 156
gacacggcct tttcg                                                   15

<210> SEQ ID NO 157
<211> LENGTH: 17
<212> TYPE: DNA
<213> ORGANISM: Homo sapiens

<400> SEQUENCE: 157
ccagcagctg accatgg                                                 17

<210> SEQ ID NO 158
<211> LENGTH: 15
<212> TYPE: DNA
<213> ORGANISM: Homo sapiens
```

```
<400> SEQUENCE: 158
gaaatcgacc ctcgg                                             15

<210> SEQ ID NO 159
<211> LENGTH: 14
<212> TYPE: DNA
<213> ORGANISM: Homo sapiens

<400> SEQUENCE: 159
gcatgttgtg gatg                                              14

<210> SEQ ID NO 160
<211> LENGTH: 16
<212> TYPE: DNA
<213> ORGANISM: Homo sapiens

<400> SEQUENCE: 160
gcagagactt tcatgc                                            16

<210> SEQ ID NO 161
<211> LENGTH: 18
<212> TYPE: DNA
<213> ORGANISM: Homo sapiens

<400> SEQUENCE: 161
ataacagcag gtgactgg                                          18

<210> SEQ ID NO 162
<211> LENGTH: 14
<212> TYPE: DNA
<213> ORGANISM: Homo sapiens

<400> SEQUENCE: 162
gaacccactt ctgc                                              14

<210> SEQ ID NO 163
<211> LENGTH: 14
<212> TYPE: DNA
<213> ORGANISM: Homo sapiens

<400> SEQUENCE: 163
gacacttgct gctg                                              14

<210> SEQ ID NO 164
<211> LENGTH: 15
<212> TYPE: DNA
<213> ORGANISM: Homo sapiens

<400> SEQUENCE: 164
ccacttctgc ttggg                                             15

<210> SEQ ID NO 165
<211> LENGTH: 15
<212> TYPE: DNA
<213> ORGANISM: Homo sapiens

<400> SEQUENCE: 165
ctgcaagtac gttcg                                             15

<210> SEQ ID NO 166
<211> LENGTH: 22
<212> TYPE: DNA
<213> ORGANISM: Homo sapiens
```

```
<400> SEQUENCE: 166
tcccttatga tgccagcaag tg                                              22

<210> SEQ ID NO 167
<211> LENGTH: 14
<212> TYPE: DNA
<213> ORGANISM: Homo sapiens

<400> SEQUENCE: 167
ccagcaatga cagc                                                       14

<210> SEQ ID NO 168
<211> LENGTH: 14
<212> TYPE: DNA
<213> ORGANISM: Homo sapiens

<400> SEQUENCE: 168
gggaaagctg aggc                                                       14

<210> SEQ ID NO 169
<211> LENGTH: 15
<212> TYPE: DNA
<213> ORGANISM: Homo sapiens

<400> SEQUENCE: 169
tcgagggaaa gctga                                                      15

<210> SEQ ID NO 170
<211> LENGTH: 14
<212> TYPE: DNA
<213> ORGANISM: Homo sapiens

<400> SEQUENCE: 170
cctcgaggga aagc                                                       14

<210> SEQ ID NO 171
<211> LENGTH: 14
<212> TYPE: DNA
<213> ORGANISM: Homo sapiens

<400> SEQUENCE: 171
gggctggtgt ggtg                                                       14

<210> SEQ ID NO 172
<211> LENGTH: 16
<212> TYPE: DNA
<213> ORGANISM: Homo sapiens

<400> SEQUENCE: 172
gaacagggct ggtgtg                                                     16

<210> SEQ ID NO 173
<211> LENGTH: 14
<212> TYPE: DNA
<213> ORGANISM: Homo sapiens

<400> SEQUENCE: 173
gaacagggct ggtg                                                       14

<210> SEQ ID NO 174
<211> LENGTH: 14
<212> TYPE: DNA
<213> ORGANISM: Homo sapiens
```

-continued

```
<400> SEQUENCE: 174
agagcgcgaa cagg                                                       14

<210> SEQ ID NO 175
<211> LENGTH: 15
<212> TYPE: DNA
<213> ORGANISM: Homo sapiens

<400> SEQUENCE: 175
gagagcgcga acagg                                                      15

<210> SEQ ID NO 176
<211> LENGTH: 15
<212> TYPE: DNA
<213> ORGANISM: Homo sapiens

<400> SEQUENCE: 176
cgagagcgcg aacag                                                      15

<210> SEQ ID NO 177
<211> LENGTH: 15
<212> TYPE: DNA
<213> ORGANISM: Homo sapiens

<400> SEQUENCE: 177 ccccctggctc ggggg                                                     15

<210> SEQ ID NO 178
<211> LENGTH: 13
<212> TYPE: DNA
<213> ORGANISM: Homo sapiens

<400> SEQUENCE: 178
ccctggctcg ggg                                                        13

<210> SEQ ID NO 179
<211> LENGTH: 14
<212> TYPE: DNA
<213> ORGANISM: Homo sapiens

<400> SEQUENCE: 179 ccccctggctc gggg                                                      14

<210> SEQ ID NO 180
<211> LENGTH: 14
<212> TYPE: DNA
<213> ORGANISM: Homo sapiens

<400> SEQUENCE: 180 tcccccctggc tcgg                                                      14

<210> SEQ ID NO 181
<211> LENGTH: 14
<212> TYPE: DNA
<213> ORGANISM: Homo sapiens

<400> SEQUENCE: 181 ctcccccctgg ctcg                                                      14

<210> SEQ ID NO 182
<211> LENGTH: 16
<212> TYPE: DNA
<213> ORGANISM: Homo sapiens
```

```
<400> SEQUENCE: 182
tgcgcttccg cttcac                                                    16

<210> SEQ ID NO 183
<211> LENGTH: 14
<212> TYPE: DNA
<213> ORGANISM: Homo sapiens

<400> SEQUENCE: 183
cctcgatgcg cttc                                                      14

<210> SEQ ID NO 184
<211> LENGTH: 14
<212> TYPE: DNA
<213> ORGANISM: Homo sapiens

<400> SEQUENCE: 184
gatggcctcg atgc                                                      14

<210> SEQ ID NO 185
<211> LENGTH: 15
<212> TYPE: DNA
<213> ORGANISM: Homo sapiens

<400> SEQUENCE: 185
ggatggcctc gatgc                                                     15

<210> SEQ ID NO 186
<211> LENGTH: 17
<212> TYPE: DNA
<213> ORGANISM: Homo sapiens

<400> SEQUENCE: 186
atggcctcga tgcgctt                                                   17

<210> SEQ ID NO 187
<211> LENGTH: 14
<212> TYPE: DNA
<213> ORGANISM: Homo sapiens

<400> SEQUENCE: 187
tcagcagggc cagg                                                      14

<210> SEQ ID NO 188
<211> LENGTH: 17
<212> TYPE: DNA
<213> ORGANISM: Homo sapiens

<400> SEQUENCE: 188
gcaaagttca gcagggc                                                   17

<210> SEQ ID NO 189
<211> LENGTH: 16
<212> TYPE: DNA
<213> ORGANISM: Homo sapiens

<400> SEQUENCE: 189
ggcaaagttc agcagg                                                    16

<210> SEQ ID NO 190
<211> LENGTH: 18
<212> TYPE: DNA
<213> ORGANISM: Homo sapiens
```

```
<400> SEQUENCE: 190
gtggcaaagt tcagcagg                                              18

<210> SEQ ID NO 191
<211> LENGTH: 14
<212> TYPE: DNA
<213> ORGANISM: Homo sapiens

<400> SEQUENCE: 191
gtggcaaagt tcag                                                  14

<210> SEQ ID NO 192
<211> LENGTH: 18
<212> TYPE: DNA
<213> ORGANISM: Homo sapiens

<400> SEQUENCE: 192
gaccgtggca aagttcag                                              18

<210> SEQ ID NO 193
<211> LENGTH: 15
<212> TYPE: DNA
<213> ORGANISM: Homo sapiens

<400> SEQUENCE: 193
agagaggctg accgt                                                 15

<210> SEQ ID NO 194
<211> LENGTH: 17
<212> TYPE: DNA
<213> ORGANISM: Homo sapiens

<400> SEQUENCE: 194
gacagagaga ggctgac                                               17

<210> SEQ ID NO 195
<211> LENGTH: 15
<212> TYPE: DNA
<213> ORGANISM: Homo sapiens

<400> SEQUENCE: 195
acagagagag gctga                                                 15

<210> SEQ ID NO 196
<211> LENGTH: 15
<212> TYPE: DNA
<213> ORGANISM: Homo sapiens

<400> SEQUENCE: 196
gtggacagag agagg                                                 15

<210> SEQ ID NO 197
<211> LENGTH: 18
<212> TYPE: DNA
<213> ORGANISM: Homo sapiens

<400> SEQUENCE: 197
caagtggaca gagagagg                                              18

<210> SEQ ID NO 198
<211> LENGTH: 16
<212> TYPE: DNA
<213> ORGANISM: Homo sapiens
```

```
<400> SEQUENCE: 198
tcttcttgat gtggcc                                        16

<210> SEQ ID NO 199
<211> LENGTH: 17
<212> TYPE: DNA
<213> ORGANISM: Homo sapiens

<400> SEQUENCE: 199
ccctcttctt cttgatg                                       17

<210> SEQ ID NO 200
<211> LENGTH: 14
<212> TYPE: DNA
<213> ORGANISM: Homo sapiens

<400> SEQUENCE: 200
caccctcttc ttct                                          14

<210> SEQ ID NO 201
<211> LENGTH: 17
<212> TYPE: DNA
<213> ORGANISM: Homo sapiens

<400> SEQUENCE: 201
atggatttct ttggcat                                       17

<210> SEQ ID NO 202
<211> LENGTH: 13
<212> TYPE: DNA
<213> ORGANISM: Homo sapiens

<400> SEQUENCE: 202
ggatttcttt ggc                                           13

<210> SEQ ID NO 203
<211> LENGTH: 18
<212> TYPE: DNA
<213> ORGANISM: Homo sapiens

<400> SEQUENCE: 203
aagttggact ctcttctc                                      18

<210> SEQ ID NO 204
<211> LENGTH: 18
<212> TYPE: DNA
<213> ORGANISM: Homo sapiens

<400> SEQUENCE: 204
taagttggac tctcttct                                      18

<210> SEQ ID NO 205
<211> LENGTH: 16
<212> TYPE: DNA
<213> ORGANISM: Homo sapiens

<400> SEQUENCE: 205
gacctaagtt ggactc                                        16

<210> SEQ ID NO 206
<211> LENGTH: 18
<212> TYPE: DNA
<213> ORGANISM: Homo sapiens
```

-continued

<400> SEQUENCE: 206
tttctagacc taagttgg                                                   18

<210> SEQ ID NO 207
<211> LENGTH: 18
<212> TYPE: DNA
<213> ORGANISM: Homo sapiens

<400> SEQUENCE: 207
ctgatttcta gacctaag                                                   18

<210> SEQ ID NO 208
<211> LENGTH: 17
<212> TYPE: DNA
<213> ORGANISM: Homo sapiens

<400> SEQUENCE: 208
gaagcagtaa ttggtgt                                                    17

<210> SEQ ID NO 209
<211> LENGTH: 15
<212> TYPE: DNA
<213> ORGANISM: Homo sapiens

<400> SEQUENCE: 209
ggaatcatca tgagg                                                      15

<210> SEQ ID NO 210
<211> LENGTH: 15
<212> TYPE: DNA
<213> ORGANISM: Homo sapiens

<400> SEQUENCE: 210
gggaatcatc atgag                                                      15

<210> SEQ ID NO 211
<211> LENGTH: 15
<212> TYPE: DNA
<213> ORGANISM: Homo sapiens

<400> SEQUENCE: 211
ggttgtcgag ccggt                                                      15

<210> SEQ ID NO 212
<211> LENGTH: 17
<212> TYPE: DNA
<213> ORGANISM: Homo sapiens

<400> SEQUENCE: 212
gtcctcccaa catagta                                                    17

<210> SEQ ID NO 213
<211> LENGTH: 14
<212> TYPE: DNA
<213> ORGANISM: Homo sapiens

<400> SEQUENCE: 213
gggtcctccc aaca                                                       14